United States Patent
Huang et al.

(10) Patent No.: US 8,845,905 B2
(45) Date of Patent: Sep. 30, 2014

(54) POLYPYRROLE COPOLYMER NANOPARTICLES-BASED COMPOSITIONS AND METHODS FOR DETECTING LEAD IONS

(75) Inventors: Mei-rong Huang, Shanghai (CN); Xiao-tian Fu, Shanghai (CN); Xin-Gui Li, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 13/821,391

(22) PCT Filed: Mar. 19, 2012

(86) PCT No.: PCT/CN2012/072536
§ 371 (c)(1),
(2), (4) Date: Mar. 7, 2013

(87) PCT Pub. No.: WO2013/138978
PCT Pub. Date: Sep. 26, 2013

(65) Prior Publication Data
US 2014/0183062 A1   Jul. 3, 2014

(51) Int. Cl.
*C02F 1/42* (2006.01)
*C02F 1/62* (2006.01)
*G01N 27/333* (2006.01)

(52) U.S. Cl.
CPC .................................. *G01N 27/3335* (2013.01)
USPC ........................... 210/688; 210/674; 525/186

(58) Field of Classification Search
USPC ....................................................... 525/58
See application file for complete search history.

(56) References Cited

U.S. PATENT DOCUMENTS

2009/0277805 A1   11/2009   Amemiya et al.

FOREIGN PATENT DOCUMENTS

| CN | 101338030 | 1/2009 |
|---|---|---|
| CN | 101907593 | 12/2010 |
| WO | WO-03/104787 | 12/2003 |

OTHER PUBLICATIONS

Li et al. J. Phys. Chem. C 2009, 113, 21586-21595.*
Borraccino et al. Sensors and Actuators B, 1992, 7, 535-539.*
A. Michalska, A. Hulanicki, A. Lewenstam. All-Solid-State Potentiometric Sensors for Potassium and Sodium Based on Poly(pyrrole) Solid Contact. Michrochem J, 57, 59-64 (1997).
Ambacha F, Moges G, Chandravanshi B S, Tetrachloroferrate(iii)-Selective Liquid Membrane Electrode Based on Crystal Violet. Mikrochim Acta 124, 63-71 (1996).
C. C. Young, Evolution of Blood Chemistry Analyzers Based on Ion Selective Electrodes, Journal of Chemical Education, vol. 74, No. 2, Feb. 1997.
Carlisle J C, Dowling K C, Siegel D M, Alexeeff G V. A blood lead benchmark for assessing risks from childhood lead exposure. J Environ Sci Health A (2009), 44, 1200-1208.
Ceresa, A.; Bakker, E.; Hattendorf, B.; Gunther, D.; Pretsch, E. Potentiometric polymeric membrane electrodes for measurement of environmental samples at trace levels: new requirements for selectivities and measuring protocols, and comparison with ICPMS. Anal Chem 2001, 73, 343-351.

(Continued)

*Primary Examiner* — Vu A Nguyen
(74) *Attorney, Agent, or Firm* — Foley & Lardner LLP

(57) ABSTRACT

Compositions containing vinyl polymers and ionophores selective for lead ions (e.g., polypyrrole copolymers), and methods for making these compositions are disclosed herein. The compositions can, for example, be used for detecting lead ions in a sample.

61 Claims, 9 Drawing Sheets

(56) References Cited

OTHER PUBLICATIONS

Coldur F, Andac M, Isildak I, Saka T. A micro-sized PVC membrane Li+-selective electrode without internal filling solution and its medical applications. Journal of Electroanalytical Chemistry 626 (2009) 30-35.

Developments in the Field of Conducting and Non-conducting Polymer Baseed Potentiometric Membrane Sensors for Ions Over the Past Decade, Sensors 2008, 8, 2331-2412.

Faith Coldur, Muberra Andac, Ibrahim Isildak. Flow-injection potentiometric applications of solid state Li+ selective electrode in biological and pharmaceutical samples. J Solid State Electrochem (2010) 14:2241-2249.

Faridbod, F.; Ganjali, M. R.; Larijani, B.; Hosseini, M.; Alizadeh, K.; Norouzi, P. Highly Selective and Sensitive Asymmetric Lead Microsensor Based on 5,5,dithiobis(2-nitrobenzoic acid) as an Excellent Hydrophobic Neutral Carrier for Nano Level Monitoring of Lead in Real Samples. Int. J. Electrochem. Sci., 4 (2009) 1528-1540.

Francesco Corica, Andrea Corsonello, Riccardo lentile, Domenico Cucinotta, Antonio Di Benedetto, Francesco Perticone, Ligia J. Dominguez, Maria Barbagallo. Serum Ionized Magnesium Levels in Relation to Metabolic Syndrome in Type 2 Diabetic Patients. J Am college of Nutrition, vol. 25, No. 3, 210-215 (2006).

Ghanei-Motlagh M, Taher M A, Saheb V, Fayazi M, Sheikhshoaie I. Theoretical and practical investigations of copper ion selective electrode with polymeric membrane based on ,N,N'-(2,2-dimethylpropane-1,3-diyl)-bis(dihydroxyacetophenone), Electrochim Acta 2011, 56, 5376-5385.

Gilbert S G, Weiss B. A rational for lowering the blood lead action level from 10 to 2 ug/dL. Neurotoxicology 2006, 27(5), 693-701.

Gupta K. C., D'Arc M. J. Lead(II) ion selective electrodes based on diphenylmethyl-N-Phenylhydroxamic acid ionophore in cyanocopolymer matrix. IEEE Sensors J. 2001, 4(1), 275-282.

Hassan Ali Zamani, Ghadir Rajabzadeh, Mahbobeh Masrornia, Azam Dejbord, Mohammed Reza Ganjali, Nasim Seifi. Determination of Cr3 ions in biological and environmental samples by a chromium (III) membrane sensor based on 5-amino-1-phenyl-1H-pyrazole-4-carboxamide. Desalination 249 (2009) 560-565.

Huang M R, Rao X W, Li X G, Ding Y B. Lead ion-selective electrodes based on polyphenylenediamine as unique solid ionophores. Talanta 85 (2011) 1575-1584.

International Search Report and Written Opinion from corresponding application No. PCT/CN2012/072536 dated Dec. 27, 2012.

Kebede L. Gemene, Eric Bakker, Measurement of total calcium by flash choronopotentiometry at polymer membrane ion-selective electrodes, Anal Chim Acta 648 (2009) 240-245.

Li X G, Ma X L, Huang M R. Lead(II) ion-selective electrode based on polyaminoanthraquinone particles with intrinsic conductivity. Talanta 78 (2009) 498-505.

Lisak G, Grygolowicz-Pawlak E, Mazurkiewicz M, Malinowska E, Sokalski T, Bobacka J, Lewenstam A. New polyacrylate-based lead(ii) ion-selective electrodes. Microchim Acta 2009, 164, 293-297.

M. R. Ganjali et al. Lutetium (III) Ions Determination in Biological and Environmental Samples by a Lutetium(III) Sensor Based on N,N1-bis(2-Pyridinecarboxamide)-1,3-benzene as a Sensing Material, downloaded by Tongji University on Jul. 14, 2011.

Michalska A, Wojciechowski M, Bulska E, Mieczkowski J, Maksymiuk K. Poly(n-butyl acrylate) based lead (ii) selective electrodes. Talanta 79 (2009) 1247-1251.

Ouyang S F, Wu P P, Li Z H. The analysis of 2815 children's blood lead assay results. J Clin Experimental Medicine 2011, 10(1), 63-64. (English translation).

Polymerized Nile Blue derivatives for plasticizer-free fluorescent ion optode microsphere sensors, Analytica Chimica Acta, vol. 599, Issue 1, Sep. 5, 2007.

Privett B J, Shin J H, Schoenfisch M H. Electrochemical sensor. Anal Chem 2010, 82, 4723-4741.

Revisions to the Evaluation of Lead. NSF/ANSI Standard 61-2007a. http://www.nsf.org/business/water_distribution/pdf/AnnexF.Pdf.

Sokalski T, Ceresa A, Fibbioli M, Zwicki T, Bakker E, Pretsch E. Lowering the Detection Limit of Solvent Polymeric Ion-Selective Membrane Electrodes. 2. Influence of Composition of Sample and Internal Eletrolyte Solution. Anal Chem 1999, 71, 1210-1214.

Sokalski T, Ceresa A, Zwicki T, Pretsch E. Large Improvement of the Lower Detection Limit of Ion-Selective Polymer Membrane Electrodes. J Am Chem Soc 1997, 119, 11347-11348.

Sonika Tyagi, Himanshu Agarwal, Saiqu Ikram. A dynamic electrochemical sensor for europium(III). Indian J Chem 2010, 49, 1325-133.

Sutter J, Radu A, Peper S, Bakker E, Pretsch E. Solid-contact polymeric membrane electrodes with detection limits in the subnanomolar range. Anal Chim Acta 523 (2004) 53-59.

Uhlig A, Lindner E, Teutloff C, Schnakenberg U, Hintsche R. Miniaturized Ion-Selective Chip Electrode for Sensor Application. Anal Chem 1997, 69, 4032-4038.

\* cited by examiner

POLYPYRROLE COPOLYMER NANOPARTICLES-BASED COMPOSITIONS AND METHODS FOR DETECTING LEAD IONS

CROSS-REFERENCE TO RELATED APPLICATIONS

This application is a U.S. National Stage of International Application Serial No. PCT/CN2012/072536, filed on Mar. 19, 2012, the entire disclosure of which is hereby incorporated by reference for all purposes in its entirety as if fully set forth herein.

BACKGROUND OF THE INVENTION

Lead is a heavy metal found naturally in the environment as well as in many common consumer products. Although low levels of lead exposure are not thought to be harmful in adults, they can result in deficits in intellectual or cognitive development and IQ reduction in infants and children. At higher levels, lead exposure can cause seizures, coma, and even death. Therefore, early detection and prevention of lead exposure are important, especially for infants and teenagers.

SUMMARY OF THE INVENTION

Some embodiments disclosed herein provide a composition having a polypyrrole copolymer and a vinyl polymer, wherein the polypyrrole copolymer includes at least one optionally substituted pyrrole as a first monomer unit and at least one optionally substituted 2-hydroxy-5-sulfonic aniline as a second monomer unit.

In some embodiments, the first monomer unit is represented by Formula I:

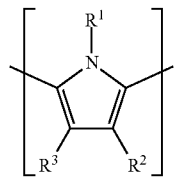

In some embodiments, $R^1$, $R^2$, and $R^3$ are each independently selected hydrogen, halogen, $C_{1-6}$ alkyl, cycloalkyl, aryl, alkylenyl, and alkoxyl. In some embodiments, $R^1$, $R^3$, and $R^3$ are each independently hydrogen. In some embodiments, $R^2$ and $R^3$ are the same.

In some embodiments, the second monomer unit is represented by Formula II:

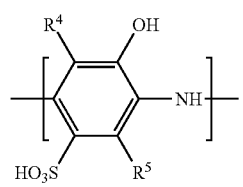

In some embodiments, $R^4$ is hydrogen or an electron-donating group, and $R^5$ is hydrogen or an electron-donating group. In some embodiments, $R^4$ and $R^5$ are each independently hydrogen.

In some embodiments, the electron-donating group is $C_{1-6}$ alkyl or alkoxyl.

In some embodiments, the polypyrrole copolymer includes at least about 10% of the first monomer unit by mole. In some embodiments, the polypyrrole copolymer includes about 50% of the first monomer unit by mole. In some embodiments, the polypyrrole copolymer has a molar ratio of the first monomer unit to the second monomer unit from about 10:90 to about 90:10. In some embodiments, the polypyrrole copolymer has a molar ratio of the first monomer unit to the second monomer unit about 50:50.

In some embodiments, the polypyrrole copolymer is present as nanoparticles. In some embodiments, the nanoparticles have an average size of about 20 nm to about 450 nm. In some embodiments, the nanoparticles have an average size of about 60 nm to about 100 nm. In some embodiments, the nanoparticles have an average size of about 30 nm to about 45 nm.

In some embodiments, the composition is in the form of a film, a membrane, a foil, or a combination thereof.

In some embodiments, the vinyl polymer is selected from polyvinyl fluoride (PVF); polyvinyl acetate (PVAc); polyvinylidene fluoride (PVDF); polyvinylidene chloride (PVDC); polytetrafluoroethylene (PTFE); polyacrylate; polyacrylic acid; a copolymer of vinyl chloride; and any combination thereof, wherein the copolymer of vinyl chloride includes no more than 50% by weight of one or more co-monomers and the one or more co-monomers are vinyl acetate or vinyl alcohol.

In some embodiments, the vinyl polymer is a copolymer of vinyl chloride and vinyl acetate. In some embodiments, the vinyl polymer is a partially hydrolysed vinyl chloride-vinyl acetate copolymer. In some embodiments, the vinyl polymer is a terpolymer of vinyl chloride, vinyl acetate and hydroxyalkyl acrylate. In some embodiments, the vinyl polymer is a copolymer of vinyl chloride, vinyl acetate and vinyl alcohol.

In some embodiments, the vinyl polymer includes about 50% to about 90% vinyl chloride by weight. In some embodiments, the vinyl polymer includes about 3% to about 50% vinyl acetate by weight.

In some embodiments, the composition is substantially plasticizer-free.

Some embodiments disclosed herein provide a polymeric membrane for ion sensitive measurement having a vinyl polymer and a polypyrrole copolymer, where the polypyrrole copolymer includes at least one optionally substituted pyrrole as a first monomer unit and at least one optionally substituted 2-hydroxy-5-sulfonic aniline as a second monomer unit.

In some embodiments, the first monomer unit is represented by Formula I:

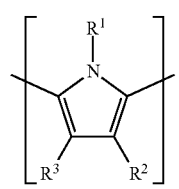

In some embodiments, $R^1$, $R^2$, and $R^3$ are each independently selected from hydrogen, halogen, $C_{1-6}$ alkyl, cycloalkyl, aryl, alkylenyl, and alkoxyl.

In some embodiments, the second monomer unit is represented by Formula II:

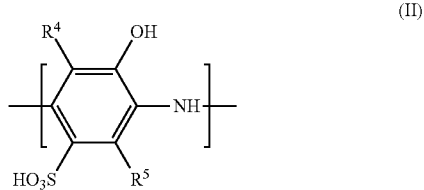

In some embodiments, $R^4$ is hydrogen or an electron-donating group, and $R^5$ is hydrogen or an electron-donating group.

In some embodiments, the polymeric membrane has about 0.1% to about 10% the polypyrrole copolymer by weight. In some embodiments, the polymeric membrane has about 3% the polypyrrole copolymer by weight.

In some embodiments, the polymeric membrane comprises one or more ion exchangers. In some embodiments, the polymeric membrane has about 0.1% to about 10% the one or more ion exchangers by weight. In some embodiments, the one or more ion exchangers are selected from sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl]borate (NaTFPB), sodium tetrakis[3,5-bis(perfluorohexyl)phenyl]borate (NaPFHPB), and any combination thereof.

In some embodiments, the polymeric membrane has an average thickness of about 40 μm to about 200 μm. In some embodiments, the polymeric membrane has an average thickness of about 120 μm.

In some embodiments, the ion sensitive measurement is a potentiometric measurement.

In some embodiments, the polymeric membrane has an operating lifetime of more than about 1 months. In some embodiments, the polymeric membrane has an operating lifetime of more than about 3 months. In some embodiments, the polymeric membrane has an operating lifetime of more than about 6 months.

Some embodiments disclosed herein provide a sensor for measuring lead ions, where the sensor includes a lead ion-selective electrode, wherein the lead ion-selective electrode comprises a vinyl polymer and a polypyrrole copolymer, wherein the polypyrrole copolymer includes at least one optionally substituted pyrrole as a first monomer unit and at least one optionally substituted 2-hydroxy-5-sulfonic aniline as a second monomer unit.

In some embodiments, the lead ion-selective electrode includes one or more ion exchangers. In some embodiments, the sensor further includes a reference electrode.

Some embodiments disclosed herein provide a method for detecting lead ions in a sample, the method includes: providing a sample suspected of containing one or more lead ions; contacting the sample with a sensor, wherein the sensor includes a reference electrode and a lead ion-selective electrode, wherein the lead ion-selective electrode comprises a vinyl polymer and one or more ionophores selective for lead ions; and measuring an electromotive force (EMF) between the reference electrode and the lead ion-selective electrode, wherein the one or more ionophores comprise a polypyrrole copolymer, wherein the polypyrrole copolymer includes at least one optionally substituted pyrrole as a first monomer unit and at least one optionally substituted 2-hydroxy-5-sulfonic aniline as a second monomer unit.

In some embodiments, the sensor is potentiometric and functions substantially logarithmic. In some embodiments, the concentration of lead ions in the sample correlates with the EMF measured.

In some embodiments, the concentration of lead ions in the sample positively correlates with the EMF measured. In some embodiments, the measured EMF is greater in the presence of lead ions than in the absence of lead ions.

In some embodiments, the concentration of the lead ions in the sample is about $10^{-6}$ M to about $10^{-13}$ M. In some embodiments, the concentration of the lead ions in the sample is about $10^{-9}$ M to about $10^{-13}$ M. In some embodiments, the concentration of the lead ions in the sample is about $7.9 \times 10^{-13}$ M.

In some embodiments, the sample is contacted with the sensor for no more than about 60 minutes. In some embodiments, the sample is contacted with the sensor for no more than about 20 minutes.

In some embodiments, the sample is a biological sample. In some embodiments, the biological sample is selected from whole blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, a biopsy sample, and any combination thereof. In some embodiments, the sample is a blood sample.

In some embodiments, the method further includes contacting the sensor with a regenerating agent to form a regenerated sensor. In some embodiments, the method further includes contacting a second sample suspected of containing lead ions with the regenerated copolymer. In some embodiments, the regenerating agent is selected from hydrochloric acid, nitric acid, sulfuric acid, and any combination thereof.

Some embodiments disclosed herein provide an apparatus for measuring lead ions, the apparatus has: a polymeric membrane comprising a vinyl polymer, a polypyrrole copolymer and one or more ion exchangers, wherein the polypyrrole copolymer comprises at least one optionally substituted pyrrole as a first monomer unit and at least one optionally substituted 2-hydroxy-5-sulfonic aniline as a second monomer unit.

In some embodiments, the first monomer unit is represented by Formula I:

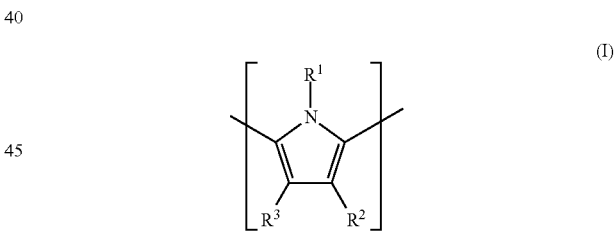

wherein $R^1$, $R^2$, and $R^3$ are each independently selected from the group consisting of hydrogen, halogen, $C_{1-6}$ alkyl, cycloalkyl, aryl, alkylenyl, and alkoxyl.

In some embodiments, the second monomer unit is represented by Formula II:

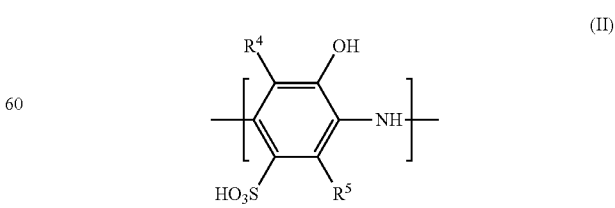

wherein $R^4$ is hydrogen or an electron-donating group, and $R^5$ is hydrogen or an electron-donating group.

In some embodiments, the polymeric membrane has about 0.1% to about 10% the polypyrrole copolymer by weight.

In some embodiments, the polymeric membrane has about 0.1% to about 10% the one or more ion exchangers by weight. In some embodiments, the one or more ion exchangers are selected from the group consisting of sodium tetraphenylborate (NaTPB), potassium tetraphenylborate (KTPB), potassium tetrakis(4-chlorophenyl)borate (KTCIPB), potassium tetrakis[3,5-bis(trifluoromethyl)phenyl]borate (KTFPB), sodium tetrakis[3,5-bis(trifluoromethyl)phenyl]borate (NaTFPB), sodium tetrakis[3,5-bis(perfluorohexyl)phenyl]borate (NaPFHPB), and any combination thereof.

In some embodiments, the polymeric membrane has an average thickness of about 40 μm to about 200 μm. In some embodiments, the polymeric membrane has an average thickness of about 120 μm.

In some embodiments, the polymeric membrane has an operating lifetime of more than about 1 month. In some embodiments, the polymeric membrane has an operating lifetime of more than about 3 months.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION OF THE INVENTION

Figure 1:
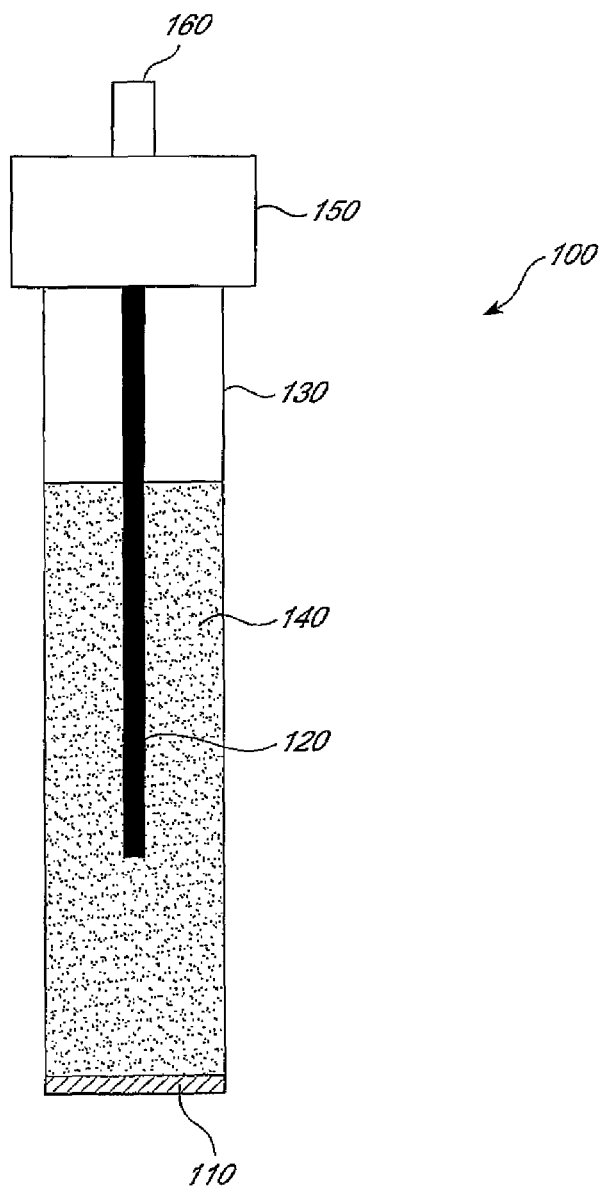
FIG. 1 depicts an embodiment of a lead ion selective electrode (Pb(II) ISE) that is in the scope of the present application.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Disclosed herein are compositions having a polypyrrole copolymer and a vinyl polymer, where the polypyrrole copolymers comprise at least one optionally substituted pyrrole as a first monomer unit and at least one optionally substituted 2-hydroxy-5-sulfonic aniline as a second monomer unit. Also disclosed herein are polymeric membranes for ion sensitive measurement, where the polymeric membranes contain a vinyl polymer and one or more ionophores selective for lead ions (sometimes written as Pb(II) or $Pb^{2+}$). The one or more ionophores, in some embodiments, have a polypyrrole copolymer and a vinyl polymer. The compositions and polymeric membranes can be used, for example, detecting metal ions, including lead ions, in a sample. The present application also includes methods of using the compositions and polymeric membranes.

DEFINITIONS

As used herein, the term "electron donating" refers to the ability of a substituent to donate electrons relative to that of hydrogen if the hydrogen atom occupied the same position in the molecule. Non-limiting examples of electron donating group include $C_{1-6}$ alkyl, alkoxyl, —$CH_3$, —$CH_2CH_3$, —OH, —$OCH_3$, —$OCH_2CH_3$, —$N(CH_3)_2$, —$N(CH_2CH_3)_2$, and —SH.

As used herein, "alkyl" refers to a straight or branched hydrocarbon chain that comprises a fully saturated (no double or triple bonds) hydrocarbon group. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and tert-butyl. Typical alkyl groups include, but are in no way limited to, methyl, ethyl, propyl, isopropyl, butyl, isobutyl, tertiary butyl, pentyl, hexyl, and the like. As used herein, the alkyl group can be substituted or unsubstituted. The term "alkylenyl" refers to a divalent alkyl linking group.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like. As used herein, the cycloalkyl group can be substituted or unsubstituted.

The halogens or halogen elements are a series of nonmetal elements from Group 17 IUPAC Style of the periodic table, comprising fluorine (F), chlorine (Cl), bromine (Br), iodine (I), and astatine (At). As used herein, "halo" or "halogen" includes fluoro, chloro, bromo, and iodo.

As used herein, "alkoxyl" refers to an —O-alkyl group. Non-limiting examples of alkoxyl groups include methoxy, ethoxy, propoxy (e.g., n-propoxy and isopropoxy), t-butoxy, and the like.

As used herein, "aryl" refers to any monocyclic, bicyclic or tricyclic carbon ring system wherein at least one ring is aromatic. In some embodiments, aryl encompasses a ring system of up to 14 carbon atoms. Examples of aryl groups include, but are not limited to, phenyl, naphthyl, tetrahydronaphthyl and indanyl.

As used herein, the "operating lifetime" of a sensing membrane in a Pb(II) selective sensor refers to the time interval between the conditioning of the sensing membrane and the moment when the slope of the potential response curve of the sensor drops below 95% of its original response slope. Accordingly, the sensing membrane is considered to be unusable when the slope of its potential response curve becomes lower than 95% of its original response slope.

As used herein, "copolymers of vinyl chloride" refers to polymers comprising vinyl chloride monomers and one or more co-monomers. In some embodiments, the copolymer of vinyl chloride include at least about 10%, at least about 20%, at least about 30%, at least about 40%, at least about 50%, at least about 60%, at least about 70%, or at least about 80%, or about 90% by weight vinyl chloride monomers. In some embodiments, the copolymer of vinyl chloride includes at most about 90%, at most about 80%, at most about 70%, at most about 60%, at most about 50%, at most about 40%, at most about 30%, at most about 20%, or at most about 10% by weight the co-monomers. Non-limiting examples of the co-monomers include vinyl acetate and vinyl alcohol.

As used herein, a composition that is "substantially plasticizer-free" refers to a composition, for example a vinyl polymer or a sensing membrane, that includes less than about 1 weight ratio percentage (i.e., 1 wt %) plasticizer(s) based on the total weight of the composition.

Abbreviations

S/cm=siemens per centimeter wt %=weight percent

EMF=electromotive force mol/L=moles per liter

Over the past decades, a number of analytical techniques have been developed for quantitatively determining trace lead ions in biological samples. For example, graphite furnace atomic absorption spectrometry (GFAAS), Erythrocyte Protoporphyrin (EP), and the European Standardized Method (ESM) are often used to measure blood lead concentrations in clinical analysis. However, the applications of these methods are limited, for example, because of expensive use charge, high maintenance of the equipment, immobility, long assay time, and/or irreproducibility.

Disclosed herein are compositions, methods, apparatus, and systems that allow low cost, portable, sensitive, reliable, and easy-to-use detection for lead ions in samples, for example samples with low concentration of lead ions. The compositions, methods, apparatus, and systems disclosed herein also have superior long lifetime for detecting lead ions.

Polypyrrole Copolymers

As used herein, "polypyrrole copolymers" refer to copolymers that have at least one optionally substituted pyrrole as a first monomer unit and at least one optionally substituted 2-hydroxy-5-sulfonic aniline as a second monomer unit. The pyrrole can, for example, be a substituted pyrrole or an unsubstituted pyrrole. In some embodiments, the pyrrole monomer unit can include, for example, zero, on; two, or three substitution.

In some embodiments, the pyrrole monomer unit (i.e., the first monomer unit) can be represented by Formula I:

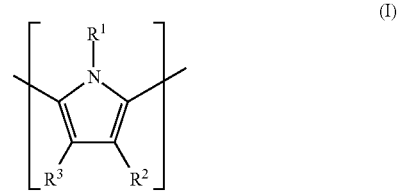

(I)

In some embodiments, $R^1$, $R^2$, and $R^3$ are each independently selected from hydrogen, halogen, $C_{1-6}$ alkyl, cycloalkyl, aryl, alkylenyl, and alkoxyl. In some embodiments, the halogen can be chloro (—Cl), bromo (—Br) or fluoro (—F). In some embodiments, one or more of $R^1$, $R^2$, and $R^3$ can be alkoxyl. In some embodiments, $R^1$, $R^2$ and $R^3$ are each $C_{1-6}$ alkyl. In some embodiments, $R^2$ and $R^3$ are each the same group. In some embodiments, at least one of $R^1$, $R^2$ and $R^3$ is hydrogen. In some embodiments, $R^2$ and $R^3$ are each independently hydrogen. In some embodiment, $R^1$ is hydrogen. In some embodiments, $R^1$, $R^2$ and $R^3$ are each the same group.

In some embodiments, the aniline monomer unit (i.e., the second monomer unit) is represented by Formula II:

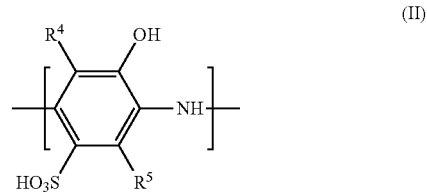

(II)

In some embodiments, $R^4$ is hydrogen or an electron-donating group, and $R^5$ is hydrogen or an electron-donating group. In some embodiments, $R^4$ and $R^5$ are independently hydrogen. In some embodiments, the electron-donating group is $C_{1-6}$ alkyl. In some embodiments, the electron-donating group is alkoxyl. In some embodiments, the first second unit is 2-hydroxy-5-sulfonic aniline represented by Formula III:

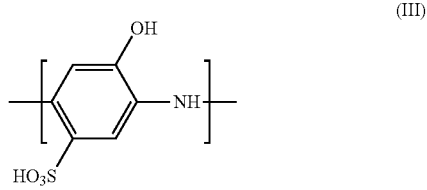

(III)

In some embodiments, the electron-donating group is —$CH_3$, —$CH_2CH_3$, —OH, —$OCH_3$, —$OCH_2CH_3$, —$N(CH_3)_2$, —$N(CH_2CH_3)_2$, or —SH.

In some embodiments, the polypyrrole copolymer is represented by Formula IV:

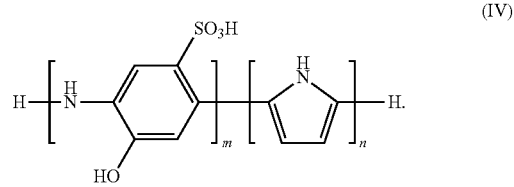

(IV)

m and n are positive integers. For examples, m and n can independently be a positive integer between 1 and 500, between 5 and 200, between 8 and 150, between 10 and 90, between 20 and 80, and between 30 and 70. In some embodiments, m and n are integers between 10 and 90. In some embodiments, m is between 10 and 90. In some embodiments, n is between 10 and 90. In some embodiments, m equals to n. In some embodiments, m does not equal to n. In some embodiments, m is 50 and n is 50.

In some embodiments, the polypyrrole copolymer is represented by Formula V:

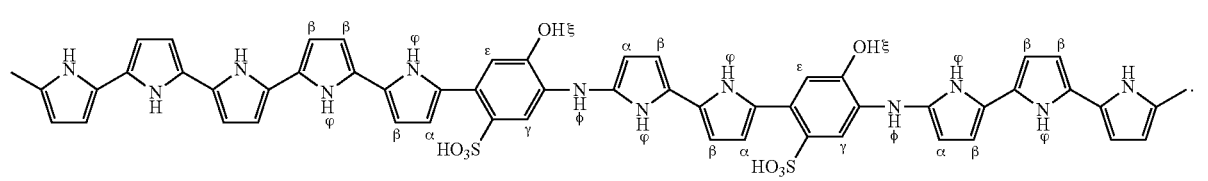

(V)

In some embodiments, the polypyrrole copolymer comprises at least about 5%, at least about 10%, at least about 20%, at least about 30%, at least about 40%, at least about 50%, at least about 60%, at least about 70%, at least about 80%, or at least about 90% of the first monomer unit by mole. In some embodiments, the polypyrrole copolymer comprises at least about 10% of the first monomer unit by mole. In some embodiments, the aniline copolymer comprises about 50% of the first monomer unit by mole. In some embodiments, the molar ratio of the first monomer unit to the second monomer unit in the aniline copolymer is about 1:99, about 5:95, about 10:90, about 20:80, about 30:70, about 40:60, about 50:50, about 60:40, about 70:30, about 80:20, about 90:10, about 95:5, about 99:1, or a range between any two of these values. In some embodiments, the molar ratio of the first monomer unit to the second monomer unit is about 50:50. A skilled artisan, guided by the teachings of the present application, can modify the relative amount of the pyrrole monomer unit and the aniline monomer unit in the copolymer to adjust the properties of the copolymer.

Some embodiments disclosed herein include submicroparticles or nanoparticles that include any one or more of the polypyrrole copolymers described herein. In some embodiments, the polypyrrole copolymer is present as nanoparticles.

The size of the polypyrrole copolymer particles can vary. For example, the polypyrrole copolymer particles can have an average diameter of about 10 nm to about 5 µm, about 20 nm to about 2 µm, about 30 nm to about 1 µm, about 40 nm to about 800 nm, about 50 nm to about 500 nm, about 100 nm to about 400 nm, about 200 nm to about 350 nm, or about 250 nm to about 300 nm. In some embodiments, the polypyrrole copolymer particles can have an average diameter of about 10 nm, about 25 nm, about 50 nm, about 100 nm, about 150 nm, about 200 nm, about 250 nm, about 300 nm, about 350 nm, about 400 nm, about 500 nm, about 600 nm, or a range between any two of these values. In some embodiments, the polypyrrole copolymer particles have an average diameter of about 50 nm to about 450 nm. In some embodiments, the polypyrrole copolymer particles have an average diameter of about 60 nm to about 100 nm. In some embodiments, the polypyrrole copolymer particles have an average diameter of about 30 nm to about 45 nm.

The polypyrrole copolymer can, in some embodiments, exhibit electrical conductivity when doped with an effective amount of dopant. The electrical conductivity of the polypyrrole copolymer can vary. For example, the polypyrrole copolymer can exhibit an electrical conductivity of about $1 \times 10^{-5}$ siemens per centimeter (i.e., S/cm), about $1 \times 10^{-2}$ S/cm, about $5 \times 10^{-3}$ S/cm, about $1 \times 10^{-3}$ S/cm, about $5 \times 10^{-2}$ S/cm, about $1 \times 10^{-2}$ S/cm, about 0.05 S/cm, about 0.1 S/cm, about 0.5 S/cm, about 1 S/cm, about 5 S/cm, about 10 S/cm, about 50 S/cm, about 100 S/cm, or a range between any two of these values. In some embodiments, the polypyrrole copolymer can exhibit a conductivity of about $1 \times 10^{-4}$ S/cm$^{-1}$ to about $1 \times 10^{-2}$ S/cm$^{-1}$. Various dopants can be used. Non-limiting examples of dopants include halogenated compounds, such as iodine, bromine, chlorine, iodine trichloride; protonic acids such as sulfuric acid, hydrochloric acid, nitric acid, perchloric acid; Lewis acids, such as aluminum trichloride, ferric trichloride, molybdenum chloride; and organic acids, such acetic acid, trifluoracetic acid, and benzenesulfonic acid. In some embodiments, the dopant is HCl, HNO$_3$, dodecylbenzenesulfonic acid (DBSA), CH$_3$COOH, HCOOH, HClO$_4$, or a combination thereof.

Methods for making the polypyrrole copolymers are also enclosed herein. A non-limiting exemplary method include: forming a composition comprising at least one oxidizing agent, at least one optionally substituted pyrrole monomer and at least one optionally substituted 2-hydroxy-5-sulfonic aniline monomer; maintaining the composition under the conditions effective to polymerize the optionally substituted pyrrole monomer and the optionally substituted 2-hydroxy-5-sulfonic aniline monomer to form a polypyrrole copolymer. In some embodiments, the optionally substituted pyrrole monomer is represented by Formula I:

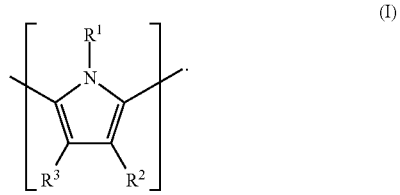

(I)

wherein R$^1$, R$^2$ and R$^3$ are as previously defined in the present application.

In some embodiments, the optionally substituted 2-hydroxy-5-sulfonic aniline monomer is represented by Formula II:

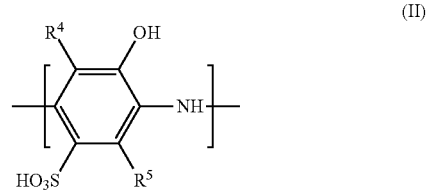

(II)

wherein R⁴ and R⁵ are as previously defined in the present application. In some embodiments, the second monomer unit is 2-hydroxy-5-sulfonic aniline represented by Formula III:

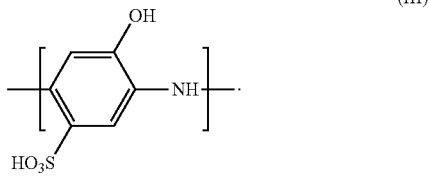

(III)

The steps and/or conditions for forming the polypyrrole copolymer are not particularly limited. Any suitable method of combining the ingredients is within the scope of the present application. For example, the oxidizing agent can be combined (e.g., mixed or dissolved) in a first solvent, and the optionally substituted pyrrole monomer and the optionally substituted 2-hydroxy-5-sulfonic aniline monomer can be combined (e.g., mixed or dissolved) in a second solvent. The solution can then be combined by dropwise or continuous addition of one of the mixtures to the other. The first and second solvents can be the same or different. In some embodiments, the first solvent is at least partially immiscible in the second solvent. In some embodiments, the oxidizing agent is soluble in the first solvent. In some embodiments, the first solvent is distilled water. In some embodiments, the first solvent is HCl. In some embodiments, both the optionally substituted pyrrole monomer and the optionally substituted 2-hydroxy-5-sulfonic aniline monomer are soluble in the second solvent. Without being bound to any specific theory, but it is believe that the solvent used for polymerization owns the ability to offer H⁺, which allows the monomer components (for example, the pyrrole monomer and the 2-hydroxy-5-sulfonic aniline monomer) to be protonated to copolymerize. In some embodiments, the second solvent is an acid aqueous medium, for example an aqueous medium containing organic and/or inorganic acids. Examples of acid include, but are not limited to, HCl, HNO$_3$, H$_2$SO$_4$, HClO$_4$, H$_3$PO$_4$, H$_5$IO$_6$, CH$_3$COOH, and any combination thereof. The pH of the aqueous medium can be, for example, less than or equal to about 6; less than or equal to about 5; less than or equal to about 4; or less than or equal to about 3. As one example, the polymerization solvent can include a protonic acid, such as 1M HCl. And various pH modifying agents can be used to adjust and/or maintain the pH of the composition to a desired pH.

Various oxidative agents can be used. Examples of the oxidizing agent include, but are not limited to, ammonium salts (such as ammonium persulfate), sodium persulfate, potassium persulfate, FeCl$_3$, potassium iodate, Na$_3$VO$_4$, benzoyl peroxide (BPO), and (NH$_4$)$_2$S$_2$O$_8$, or a combination thereof. In some embodiments, the oxidizing agent is (NH$_4$)$_2$S$_2$O$_8$.

The molar ratio of the oxidizing agent to the monomer components used to synthesize the polypyrrole copolymer can be modified, for example, to adjust the properties of the copolymer. The relative molar ratio of the oxidizing agent to the monomer components in the composition can be, for example, about 0.1:1 to about 5:1. In some embodiments, the relative molar ratio of the oxidizing agent to the monomer components is about 4.4:1.

After forming the composition having the optionally substituted pyrrole monomer, the optionally substituted 2-hydroxy-5-sulfonic aniline monomer, and the oxidizing agent, the composition can be maintained at conditions effective to polymerize the monomer components to form the polypyrrole polymer. For example, the composition can be maintained at about atmospheric pressure and a temperature of about −10° C. to about 100° C., for example, about −5° C. to about 50° C., about 0° C. to about 35° C., about 0° C. to about 26° C., or about 11° C. to about 27° C. In some embodiments, the temperature can be about 0° C. In some embodiments, the temperature can be about 14° C.

The composition having the optionally substituted pyrrole monomer, the optionally substituted 2-hydroxy-5-sulfonic aniline monomer, and oxidizing agent can be maintained at the conditions for a period of time sufficient to obtain the polypyrrole copolymer. The composition, for example, can be maintained at the conditions for about 1 hour to about 48 hours, for example about 2 hours to about 48 hours. In some embodiments, the composition is maintained at the conditions for about 24 hours.

The polypyrrole copolymer can, in some embodiments, be isolated from the composition by centrifuging the composition to obtain one or more copolymers within the precipitate. The copolymer can be subject to various other optional treatments, such as washing, doping, dedoping, and the like.

The yield of the polypyrrole copolymer using the method will vary depending upon various factors, such as the temperature and the like. In some embodiments, the method yields at least about 50%, at least about 60%, at least about 70%, at least about 80%, or at least about 90% by weight of copolymer relative to a total amount of the monomer components in the composition.

A skilled artisan will appreciate that the methods for synthesizing the polypyrrole copolymer disclosed herein are not particularly limited. For example, self-stabilized pyrrole copolymer nanoparticles have been synthesized by a chemical oxidative polymerization of pyrrole (Py) and 2-hydroxy-5-sulfonic aniline (HS) in 1 M HCl without any external template.

Vinyl Polymers

Vinyl polymers are polymers derived from vinyl monomers. Examples of vinyl polymers include, but are not limited to, polyvinyl fluoride (PVF), polyvinyl acetate (PVAc), PVA (polyvinyl alcohol), polyvinylidene fluoride (PVDF), polyvinylidene chloride (PVDC); polytetrafluoroethylene (PTFE), copolymers of vinyl chloride, and combinations thereof. In some embodiments, the copolymer of vinyl chloride comprises no more than 50% by weight of one or more co-monomers, wherein the one or more co-monomers are vinyl acetate or vinyl alcohol.

In some embodiments, the vinyl polymer can be a partially hydrolysed vinyl chloride-vinyl acetate copolymer (also called hydroxyl-functional vinyl resin). Examples of partially hydrolysed vinyl chloride-vinyl acetate copolymer include, but are not limited to, a terpolymer of vinyl chloride, vinyl acetate and ethanol (e.g., VAGD and VAGH).

In some embodiments, the vinyl polymer can be a terpolymer of vinyl chloride, vinyl acetate and hydroxyalkyl acrylate. Non-limiting examples of terpolymer of vinyl chloride, vinyl acetate and hydroxyalkyl acrylate includes terpolymers of vinyl chloride, vinyl acetate and carboxylic acid (e.g., VAGC).

Non-limiting examples of copolymer of vinyl chloride and vinyl acetate include SOLBIN C, SOLBIN CL, SOLBIN CH, SOLBIN CN, SOLBIN C5, SOLBIN M, SOLBIN MF, SOLBIN A, SOLBIN AL, SOLBIN TA5R, SOLBIN TAO, SOLBIN MK6, and SOLBIN TA2; S-LEC A, S-LEC C and S-LEC M; Vinylite VAGH, Vinylite VYHH, Vinylite VMCH, Vinylite VYHD, Vinylite VYLF, Vinylite VYNS, Vinylite VMCC, Vinylite YMCA, Vinylite VAGD, Vinylite VERR and Vinylite VROH; and DENKA VINYL 1000GKT, DENKA VINYL 1000L, DENKA VINYL 1000 CK, DENKA VINYL 1000A, DENKA VINYL 1000LK2, DENKA VINYL 1000AS, DENKA VINYL 1000MT2, DENKA VINYL 1000CSK, DENKA VINYL 1000CS, DENKA VINYL 1000GK, DENKA VINYL 1000GSK, DENKA VINYL 1000GS, DENKA VINYL 1000LT3, DENKA VINYL 1000D and DENKA VINYL 1000W.

In some embodiments, the vinyl polymer is a copolymer of vinyl chloride, which comprises vinyl chloride monomers and one or more co-monomers. The amount of vinyl chloride monomer in the vinyl polymer can vary. For example, the vinyl polymer can have about 50%, about 60%, about 70%, about 80%, about 90%, or a range between any two of these values, vinyl chloride by weight. The amount of the co-monomer(s) in the vinyl polymer can also vary. For example, the copolymer of vinyl chloride can includes at most about 90%, at most about 80%, at most about 70%, at most about 60%, at most about 50%, at most about 40%, at most about 30%, at most about 20%, about 10%, or a range between any two of these values the co-monomers by weight. Non-limiting examples of the co-monomers include vinyl acetate and vinyl alcohol.

In some embodiments, the vinyl polymer is a copolymer of vinyl chloride and vinyl acetate. In some embodiments, the vinyl polymer is a copolymer of vinyl chloride, vinyl acetate and vinyl alcohol. In some embodiments, the vinyl polymer can have about 3%, about 5%, about 10%, about 20%, about 30%, about 40%, about 50%, or a range between any two of these values vinyl acetate by weight. In some embodiments, the vinyl polymer can have about 30%, about 20%, about 10%, about 5%, about 3%, or a range between any two of these values vinyl alcohol by weight. In some embodiments, the vinyl polymer can have no more than about 30%, no more than about 20%, no more than about 10%, or no more than about 5%, vinyl alcohol by weight.

In some embodiments, the vinyl polymer is substantially plasticizer-free. Non-limiting examples of plasticizer include phthalate-based plasticizers, for example 1, 2-benzenedicarboxylic acid esters. Examples of phthalate-based plasticizers include, but are not limited to, dioctyl phthalate (DOP), di(2-ethylhexyl) phthalate (DEHP), diisononyl phthalate (DINP), di-n-butyl phthalate (DBP), benzyl butyl phthalate (BBP), diisodecyl phthalate (DIDP), di(n-octyl) phthalate (DNOP), diisooctyl phthalate (DIOP), diethyl phthalate (DEP), diisobutyl phthalate (DIBP), dimethyl phthalate (DMP), diallyl phthalate (DAP), di-n-propyl phthalate (DPP), butyl cyclohexyl phthalate (BCP), di-n-pentyl phthalate (DNPP), dicyclohexyl phthalate (DCP), di-n-hexyl phthalate (DNHP), diisohexyl phthalate (DIHxP), diisoheptyl phthalate (DIHpP), butyl decyl phthalate (BDP), n-Octyl n-decyl phthalate (ODP), di(2-Propyl Heptyl) phthalate (DPHP), diundecyl phthalate (DUP), diisoundecyl phthalate (DIUP), diisoundecyl phthalate (DTDP), diisotridecyl phthalate (DIUP), and combinations thereof.

In some embodiments, the vinyl polymer contains less than about 0.01 wt %, less than about 0.05%, less than about 0.1 wt %, less than about 0.5 wt %, less than about 0.6%, less than about 0.7%, less than about 0.8%, less than about 0.9%, or less than about 1 wt % plasticizer(s) based on the total weight of the vinyl polymer.

The methods by which the vinyl polymers are synthesized are not limited in any way. In some embodiments, the vinyl polymer is synthesized by using one or more vinyl monomers, including but not limited to, vinyl fluoride, vinyl alcohol, vinyl chloride, vinylidene chloride, and tetrafluoroethylene. In some embodiments, the vinyl polymer is synthesized using vinyl compounds with various degree of polymerization.

Compositions Including Polypyrrole Copolymers and Vinyl Polymers

Some embodiments disclosed herein provide compositions including one or more polypyrrole copolymers disclosed herein and one or more vinyl polymers disclosed herein.

The amount of the polypyrrole copolymers present in the composition is not particularly limited and can vary. For example, the composition can have about 0.1%, about 0.05%, about 0.1%, about 0.5%, about 1%, about 2%, about 3%, about 4%, about 5%, about 6%, about 7%, about 8%, about 9%, about 10%, or a range between any two of these values, the polypyrrole copolymer by weight. In some embodiments, the composition has about 0.1% to about 10% the polypyrrole copolymer by weight. In some embodiments, the composition has about 3% the polypyrrole copolymer by weight.

In addition to the vinyl polymer and the polypyrrole copolymer, the composition disclosed herein can also contain other components, including but not limited to, one or more ion exchangers. Non-limiting examples of exchangers include sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl]borate (NaTFPB), sodium tetrakis [3,5-bis(perfluorohexyl)phenyl]borate (NaPFHPB), and any combination thereof. The amount of the ion exchangers present in the composition can vary. For example, the composition can have about 0.05%, 0.1%, about 0.5%, about 1%, about 2%, about 3%, about 4%, about 5%, about 6%, about 7%, about 8%, about 9%, about 10%, or a range between any two of these values, the ion exchanger by weight.

In some embodiments, the composition is substantially plasticizer-free. In some embodiments, the composition contains less than about 0.01 wt %, less than about 0.05 wt %, less than about 0.1 wt %, less than about 0.5 wt %, less than about 0.6 wt %, less than about 0.7 wt %, less than about 0.8 wt %, less than about 0.9 wt %, less than about 1 wt %, or less than about 1.5 wt %, plasticizer(s) based on the total weight of the composition.

The composition can, in some embodiments, be in the form of a liquid that includes one or more of the polypyrrole copolymers and vinyl polymers described herein. For example, the composition can be dispersed or dissolved in a solvent. The solvent can be an organic solvent or water. The organic solvent can, for example, be a non-polar solvent, a polar aprotic solvent, a polar protic solvent, or a combination thereof. In some embodiments, the composition includes a polar aprotic solvent. Non-limiting examples of polar aprotic solvents include n-methyl-2-pyrrolidone (NMP), dimethylformamide (DMF), dimethyl sulfoxide (DMSO), and tetrahydrofuran (THF). In some embodiments, the solvent is THF.

The composition can, in some embodiments, be in the form of a solid that includes the polypyrrole copolymer and the vinyl polymer described herein. In some embodiments, a solid form of the composition can be obtained by precipitating or drying the composition from solution (e.g., solvent casting).

The compositions disclosed herein can be in various forms, including but not limited to, the form of a film, a membrane, a foil, or a combination thereof. In some embodiments, the composition is in the form of a polymeric membrane.

Apparatuses for Detecting Lead Ions

Sensing Membrane for Pb(II) Detection

Some embodiments herein provide a polymeric membrane that can be used, in some embodiments, for ion sensitive measurement. For example, the polymeric membrane can be used as a sensing membrane for ions (e.g., lead ions). The polymeric membrane, in some embodiments, comprises a vinyl polymer and one or more ionophores selective for lead ions. In some embodiments, the polymeric membrane is used as a sensing membrane for detecting Pb(II) in a sample.

In some embodiments, the ionophore comprises one or more of the polypyrrole copolymer. The polypyrrole copolymer can be any one or more of the polypyrrole copolymers described herein.

The amount of the one or more ionophores present in the polymeric membrane can vary. For example, the polymeric membrane can have about 0.05%, about 0.1%, about 0.5%, about 1%, about 2%, about 3%, about 4%, about 5%, about 6%, about 7%, about 8%, about 9%, about 10%, or a range between any two of these values, the ionophores by weight. In some embodiments, the polymeric membrane has about 0.1% to about 10% the ionophores by weight. In some embodiments, the polymeric membrane has about 3% the ionophores by weight.

In addition to the vinyl polymer and the ionophores, the polymeric membranes disclosed herein can also contain other components, including but not limited to, one or more ion exchangers. Non-limiting examples of exchangers include sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl]borate (NaTFPB), and any combinations thereof.

The thickness of the polymeric membrane can vary. For example, the polymeric membrane can have an average thickness of about 20 μm, about 30 μm, about 40 μm, about 50 μm, about 60 μm, about 70 μm, about 80 μm, about 90 μm, about 100 μm, about 120 μm, about 140 μm, about 160 μm, about 180 μm, about 200 μm, about 300 μm, or a range between any two of these values. In some embodiments, the polymeric membrane has an average thickness of about 40 μm to about 200 μm. In some embodiments, the polymeric membrane has an average thickness of about 120 μm.

Ion Selective Electrodes (ISEs)

Also enclosed herein are Pb(II) ion selective electrodes (Pb(II) ISEs) that contain the polymeric membrane disclosed herein.

FIG. 1 depicts an embodiment of a Pb(II) ISE that is within the scope of the present application. Pb(II)-ISE 100 can include sensing membrane 110, internal reference electrode 120, supporting tube 130, internal electrolyte solution 140, cap 150, and conductor wire 160. Internal reference electrode 120 is in contact with internal electrolyte solution 140 encapsulated in supporting tube 130. The sensing membrane 110 can be immersed into a sample suspected of containing one or more lead ions. Sensing membrane 110 can include any one or more of the vinyl polymer- and polypyrrole copolymer-containing composition described herein. Sensing membrane 110 can include any one or more of the polymeric membranes disclosed herein.

The Pb(II) ISE, in some embodiments, is used in conjunction with an external reference electrode to detect the presence and/or measure the concentration of lead ions in the sample. In some embodiments, both the Pb(II) ISE and the external reference electrode are contacted with the sample suspected of containing one or more lead ions to detect the presence of lead ions in the sample. The potential difference between the Pb(II) ISE and external reference electrode is, in some embodiments, a function of the concentration of lead ions in the sample.

In some embodiments, the external reference electrode is an electrode which has a stable and well-known electrode potential. In some embodiment, the external reference electrode has an internal half-cell supported in a tube containing a salt solution, the tube of salt solution being known as a salt bridge (also known as a bridge electrolyte solution). The salt bridge solution can be a concentrated equitransferent salt solution (e.g., potassium chloride and potassium nitrate). Various electrode can be used as the external reference electrode, including but not limited, to saturated calomel electrode (SCE, $Hg/Hg_2Cl_2$), silver-silver chloride electrode (Ag/AgCl), and copper-copper(II) sulfate electrode.

In some embodiments, the Pb(II) ISE and the external reference electrode are attached to an ion meter (e.g., a pH meter), where the ion meter can be used to detect an electromotive force (EMF) between the Pb(II) ISE and the external reference electrode. In some embodiments, the EMF value is proportional to the Pb(II) concentration in the sample to which the electrodes are exposed.

The operating lifetime of the polymeric sensing membrane can vary. For example, the polymeric sensing membrane can have an operating lifetime of about 1 month, about 2 months, about 3 months, about 6 months, about 7 months, abut 8 months, about 9 months, about 10 months, about 11 months, about 12 months, about 13 months, about 14 months, about 15 months, about 16 months, about 17 months, about 18 months, about 24 months, or a range between any two of these values. In some embodiments, the polymeric sensing membrane can have an operating lifetime of more than about 1 month, more than about 2 months, more than about 3 months, more than about 6 months, more than about 9 months, more than about 12 months, or more than about 18 months. In some embodiments, the polymeric sensing membrane has an operating lifetime of more than about 1 month. In some embodiments, the polymeric sensing membrane has an operating lifetime of more than about 3 months.

Also disclosed herein are sensors for measuring lead ions. The sensor can include the lead ion-selective electrode disclosed herein. In some embodiments, the sensor further includes a reference electrode.

Some embodiments disclosed herein provide an apparatus for measuring lead ions, the apparatus has: a polymeric membrane comprising a vinyl polymer, a polypyrrole copolymer and one or more ion exchangers, wherein the polypyrrole copolymer comprises at least one optionally substituted pyrrole as a first monomer unit and at least one optionally substituted 2-hydroxy-5-sulfonic aniline as a second monomer unit.

Methods for Detecting Lead Ions

Some embodiments disclosed herein include methods for detecting the presence and/or the concentration of lead ions (sometimes written as Pb (II) or $Pb^{2+}$), in a sample.

In some embodiments, the method include providing a sample suspected of containing one or more lead ions; contacting the sample with the Pb(II)-sensitive sensor disclosed herein. The Pb(II)-sensitive sensor can include a reference electrode and a lead ion-selective electrode, where the lead ion-selective electrode comprises the vinyl polymer and the one or more ionophores selective for lead ions; and measuring an electromotive force (EMF) between the reference electrode and the lead ion-selective electrode. In some embodiments, the sample is contacted with the lead ion-selective electrode. In some embodiments, the sample is contacted with the reference electrode and the lead ion-selective electrode.

The methods disclosed herein can be used for detecting the presence of lead ions and measuring the amount/concentration of lead ions in a sample. In some embodiments, the sensor is potentiometric and functions substantially logarithmic. In some embodiments, the ion sensitive measurement is a potentiometric measurement. In some embodiments, the amount and/or the concentration of the lead ions in the sample correlate with the EMF measured. In some embodiments, the amount and/or the concentration of the lead ions in the sample positively correlate with the EMF measured. In some embodiments, the relation between the concentration of lead ions and the EMF measured is logarithmic. In some embodiments, the measured EMF is greater in the presence of lead ions than in the absence of lead ions.

The methods disclosed herein can be used for detecting the presence and/or concentration of Pb(II) in various types of samples. In some embodiments, the sample can be an aqueous sample. In some embodiments, the sample can be a biological sample. Examples of biological samples include, but are not limited to, whole blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, a biopsy sample, and any combinations thereof. In some embodiments, the sample is a blood sample. In some embodiments, the sample is a clinical sample or body fluid. In some embodiments, the sample can be pretreated by e.g., digestion. In some embodiments, the sample can be an environmental sample, a food product, a medicine product, a dietary supplement, a dental hygienic composition, a cosmetic product, a biological sample, or a combination thereof. Examples of environmental sample include, but are not limited to, river water, rainwater, waste water, and combinations thereof. In some embodiments, the sample is tap water. In some embodiments, the sample is food product or a medicine product. In some embodiments, the food product is a beverage.

The concentration of lead ions in the sample can vary. The concentration of the lead ions in the sample can be about $10^{-13}$ mol/L (i.e., $10^{-11}$ M), about $5\times10^{-13}$ M, about $10^{-12}$ M, about $5\times10^{-12}$ M, about $10^{-11}$ M, about $5\times10^{-11}$ M, about $10^{-10}$ M, about $5\times10^{-10}$ M, about $10^{-9}$ M, about $5\times10^{-9}$ M, about $10^{-8}$ M, about $5\times10^{-8}$ M, about $10^{-7}$ M, about $5\times10^{-7}$ M, about $10^{-6}$ M, about $5\times10^{-6}$ M, or ranges between any two of these values. In some embodiments, the concentration of the lead iron in the sample is about $10^{-6}$ M to about $10^{-13}$ M. In some embodiments, the concentration of the lead ion is about $10^{-9}$ M to about $10^{-13}$ M. In some embodiments, the concentration of the lead ion in the sample is less than about $10^{-12}$ M, less than about $10^{-11}$ M, less than about $10^{-10}$ M, or less than about $10^{-9}$ M. In some embodiments, the concentration of the lead ion in the sample is about $7.9\times10^{-13}$ M.

The compositions and methods described herein can allow rapid detection of lead ions in a sample. For example, the minimal time needed for the sample to contact with the compositions, including the lead ion-selective electrodes disclosed herein, to allow detection of the lead ions and/or measuring of the concentration of the lead ions in the sample can be no more than about 60 minutes, no more than about 50 minutes, no more than about 40 minutes, no more than about 30 minutes, no more than about 20 minutes, no more than about 15 minutes, no more than about 10 minutes, no more than about 5 minutes, no more than 60 seconds, no more than about 30 seconds, or a range between any two of these values. In some embodiments, the minimal time needed for the sample to contact with the compositions to allow detection of the lead ions and/or measuring of the concentration of the lead ions in the sample is at most about 30 seconds, at most about 60 seconds, at most about 5 minutes, at most about 10 minute, at most about 15 minute, at most about 20 minutes, at most about 30 minutes, at most about 40 minutes, at most about 50 minute, or at most about 60 minutes.

The polymeric sensing membrane and the sensor disclosed herein can be regenerated for detecting lead ions after one or more times of use. In some embodiments, the sensor or polymeric sensing membrane can be contacted with a regenerating agent to form a regenerated sensor or polymeric sensing membrane. Various regenerating agents can be used to regenerate the sensor or the polymeric sensing membrane. Examples of regenerating agents include, but are not limited to hydrochloric acid (HCl), nitric acid ($HNO_3$), and sulfuric acid ($H_2SO_4$). In some embodiments, the regenerating agent is hydrochloric acid. In some embodiments, the methods disclosed herein include contact a sample suspected of containing lead ions with a regenerated sensor.

The sensor or polymeric sensing membrane can be repeatedly regenerated for detecting lead ions. In some embodiments, the sensor or polymeric sensing membrane is usable for detecting lead ions after being regenerated for about twice, about 3 times, about 5 times, about 8 times, about 10 times, about 15 times, about 20 times, about 25 times, or about 30 times.

EXAMPLES

Additional embodiments are disclosed in further detail in the following examples, which are not in any way intended to limit the scope of the claims.

Example 1

Polymerization of Pyrrole (Py) and
2-hydroxy-5-sulfonic aniline (HS)

Chemical oxidative polymerization of pyrrole (Py) and 2-hydroxy-5-sulfonic aniline (HS) for the synthesis of HS/Py copolypyrrole particles was carried out in a typical synthesis procedure described below.

A typical preparation procedure of the HS/Py copolypyrrole particles include: dissolving Hydroxy Sulfoaniline (HS) (0.946 g, 5 mmol) and pyrrole (Py) (0.35 mL, 5 mmol) in HCl solution (1 M, 220 mL) under magnetic stirring at 0-5° C. for about half an hour. Oxidant $(NH_4)_2S_2O_8$ (5.02 g, 22 mmol) was dissolved in HCl (1 M, 44 mL) solution at the same temperature. The $(NH_4)_2S_2O_8$ solution was dropwise added into the solution of HS/Py co-monomers in a period of 55 minutes under magnetic stirring. Copolymerization was carried out for 24 hour at 0-5° C. in atmosphere. The as-prepared products were obtained by centrifugation, and then washed with ethanol and deionized water several times until the upper layer liquid became colorless. The resulted black copolymer powder was dried under an infrared lamp for 3 days. The production yield for the HS/Py polypyrrole copolymer was 37.0%. The resulted copolymer shows 30-45 nm particle size by TEM and the pressed copolymer powder possesses a bulk electrical conductivity of $10^{-4}$ S/m measured by a two-disk method at room temperature with a UT 70A multimeter.

The reaction and nominal structure of the HS/Py polypyrrole copolymer is shown in Scheme I:

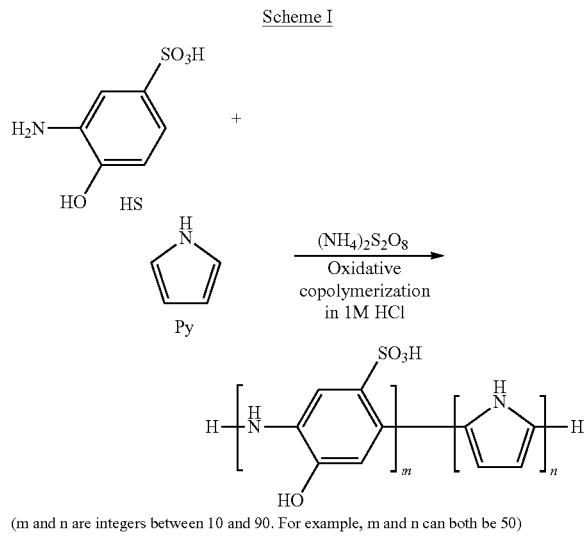

(m and n are integers between 10 and 90. For example, m and n can both be 50)

Example 2

Preparation of Pb(II) Sensing Membranes

Pb(II) sensing membranes were prepared using the typical procedure described as follows.

Py/HS nanoparticles were prepared according to the general procedure described in Example 1. 5 mg Py/HS nanoparticles, 5 mg NaTPB and 150 mg vinyl resin (Vinyl resin having a degree of polymerization of 360 (VR) (Dow Chemical Company) were added in 10 mL THF by an intermittently ultrasonic treatment for 10 minutes. The mixture was casted on a smooth Polytetrafluoroethylene (PTFE) plate, and the casted mixture was allowed to evaporate for 24 hour at room temperature. A membrane containing Py/HS nanoparticles was obtained after the evaporation of THF. The thickness of the membrane was approximately 120 μm measured by a roller type thickness gauge with the minimum scale of 10 μm.

Example 3

Assembly of Potentiometric Pb(II) Sensors

Potentiometric Pb(II) sensors were assembled using the typical procedure described as follows.

Pb(II) sensing membranes were prepared using the general procedures described in Example 2. A circular membrane of 15 mm diameter was cut out from a Pb(II) membrane and glued to one end of a plastic tube. The plastic tube was filled with $10^{-4}$ M $Pb(NO_3)_2$ solution as internal reference solution to prepare a reference electrode. The prepared electrode was conditioned in a $10^{-4}$ M $Pb(NO_3)_2$ solution for 24 hours and washed with distilled deionized water until a stable potential (drift<1 mV/5 minutes) was reached before use.

Figure 2:
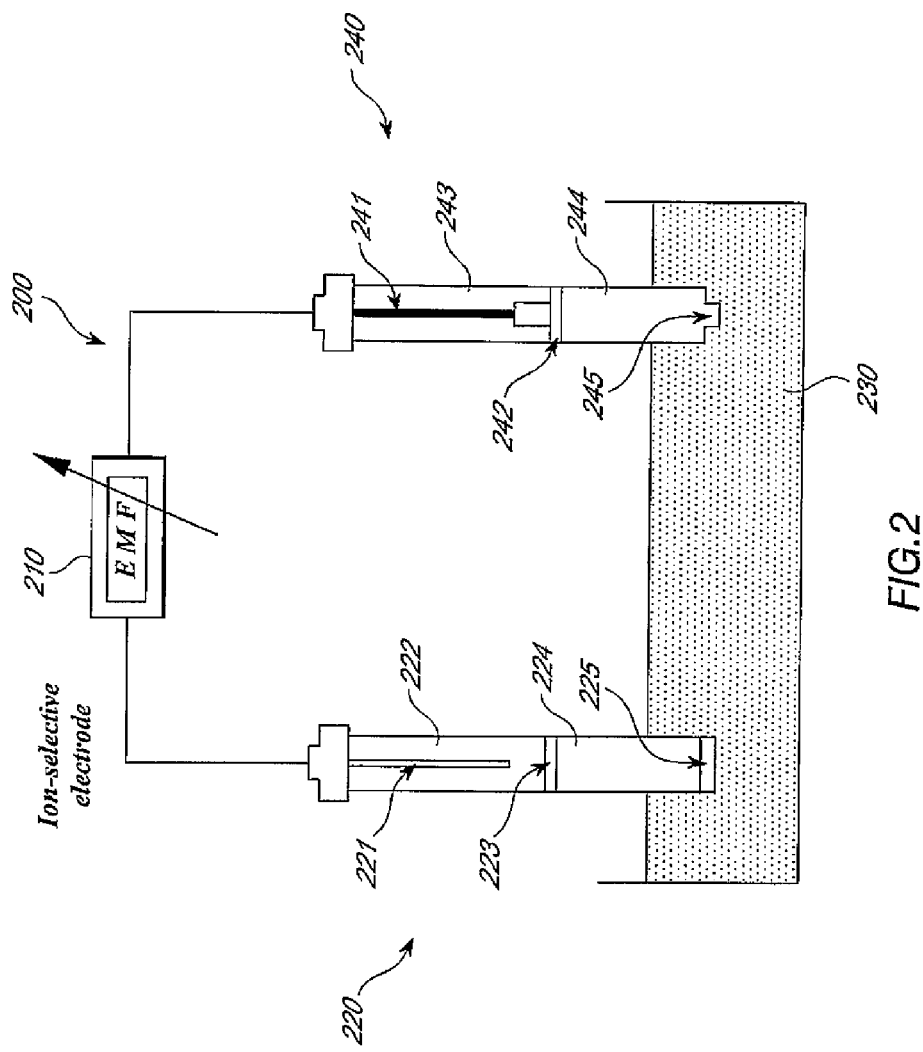
FIG. 2 shows an embodiment of a potentiometric Pb(II) sensor and the measuring circuit that is in the scope of the present application. The sensor has a Pb(II) ion-selective membrane containing vinyl polymers and ionophores selective for lead ions (e.g., polypyrrole copolymer nanoparticles).

A schematic illustration of Pb(II) selective electrode (Pb (II) ISE) 220 and external reference electrode 240 is shown in FIG. 2. In measuring circuit 200, ion meter 210 was connected with Pb(II) Pb(II) ISE 220 and external reference electrode 240 to detect the EMF between the two electrodes in detecting the presence of Pb(II) in sample solution 230 (FIG. 2).

Pb(II)-ISE 220 included Pb(II) sensing membrane 225 that was immersed into sample solution 230. Pb(II)-ISE 220 also includes internal reference electrode (Ag/AgCl) 221 that was in contact with inner reference electrolyte solution 222. Diaphragm 223 separated inner filling solution 224 and inner reference electrolyte solution 222 in Pb(II)-ISE 220. In external reference electrode 240, reference electrode $(Hg/Hg_2Cl_2)$ 241 was in contact with reference electrolyte solution 243, diaphram 242 separated reference electrolyte solution 243 and bridge electrolyte solution 244, and diaphramor capillary 245 was in contact with sample solution 230.

Example 4

Specificity of Polypyrrole Polymers to Pb(II)

Potentiometric Pb(II) sensors were assembled using the typical procedure described in Example 3. Potentiometric measurements of lead ions in a sample were performed by a PHS-3C digital pH meter in quiescent solution for at least 3 times to ensure reproductively. Activity coefficients of primary ions were thought to be 1 and thus both the activity and the concentration are the same when the lead ion concentration was below $1 \times 10^{-6}$ M. Otherwise, the activity coefficients of lead ions were calculated according to the Debye-Huckel approximation. The lower detection limit was taken as the activity of primary at the point of intersection of the extrapolated linear midrange and final low concentration level segments of the calibration plot. The response time of the electrode sensor was determined by measuring the time required to achieve a steady potential (drift<1 mV/5 minutes). pH of lead-ion solution was adjusted by 1.0 M $HNO_3$ and 1.0 M NaOH when considering the applicable pH range of the electrode sensor.

The representative electrochemical cell for electromotive force (EMP) measurement was conducted as follows:
Ag|AgCl|KCl (saturated solution)||$Pb(NO)_3$ ($1 \times 10^{-4}$ M) |Sensing Membrane|Test solution ||$KNO_3$(1M)||KCl (saturated solution)|$Hg_2Cl_2$|Hg This example shows that the aniline copolymers are highly selective for Pb(II).

Example 5

Potential Response of the Potentiometric Pb(II) Sensor

Potentiometric Pb(II) sensors were assembled using the typical procedure described in Example 3. Potentiometric measurements of lead ions in a sample were performed by a PHS-3C digital pH meter in quiescent solution. The potential response of the sensor was measured in a conventional inner reference system and the results are shown in FIG. 3.

Figure 3:
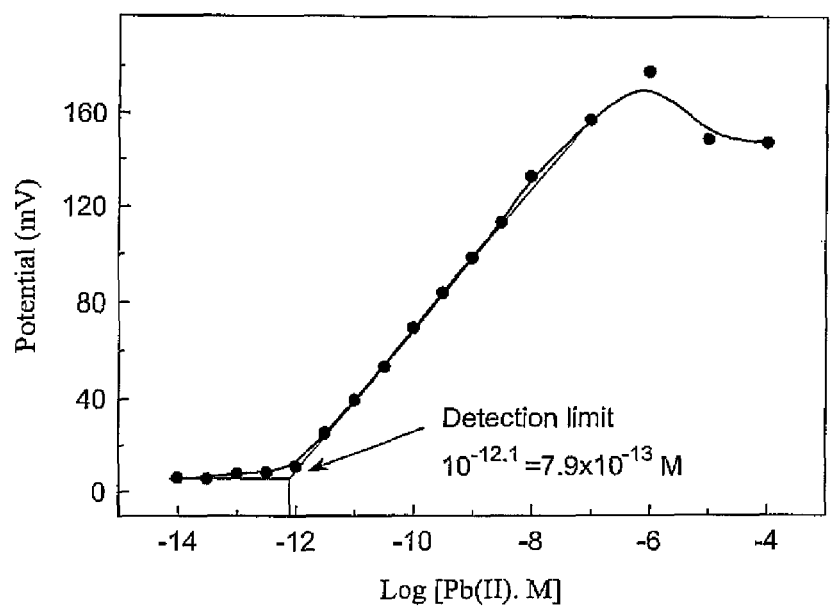
FIG. 3 shows a response curve of the potentiometric sensor.

As shown in FIG. 3, a linear Nernstian response range for Pb(II) was extended to $10^{-12}$ M and the detection limit is lowered down to $10^{-12.1}$ M when the concentration of Pb(II) in inner filling solution is $1.0 \times 10^{-4}$ M. The fitting linear analysis in the Pb(II) concentration range from $10^{-12}$ M to $10^{-7}$ M give a perfect linear relationship with a Nernstian slope of 29.7 mV/decade at a correlation coefficient of 0.9995 and standard deviation of 1.57. Wide linear range spans 6 orders of magnitude.

Figure 4:
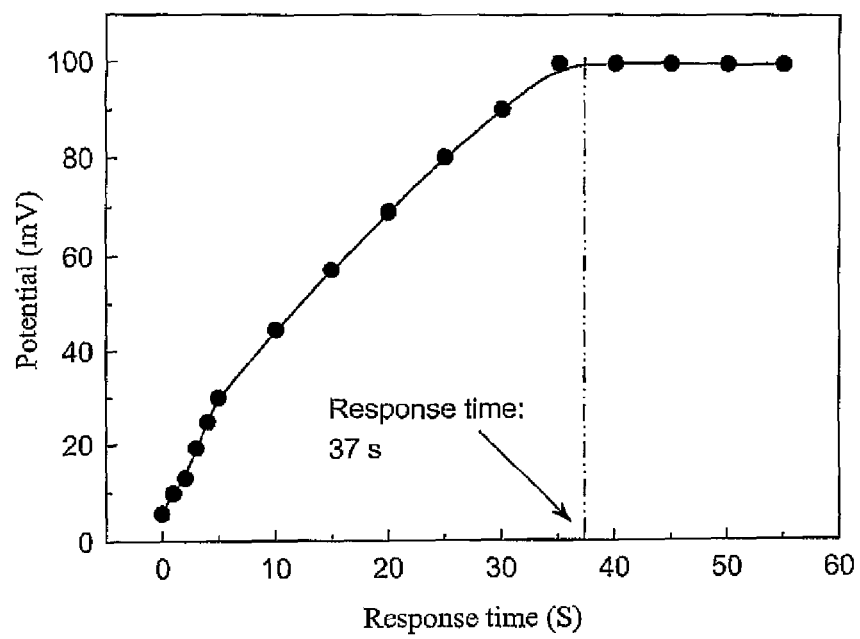
FIG. 4 shows response time of the potentiometric sensor for Pb(II) at $1.0 \times 10^{-8}$ M.
Figure 5:
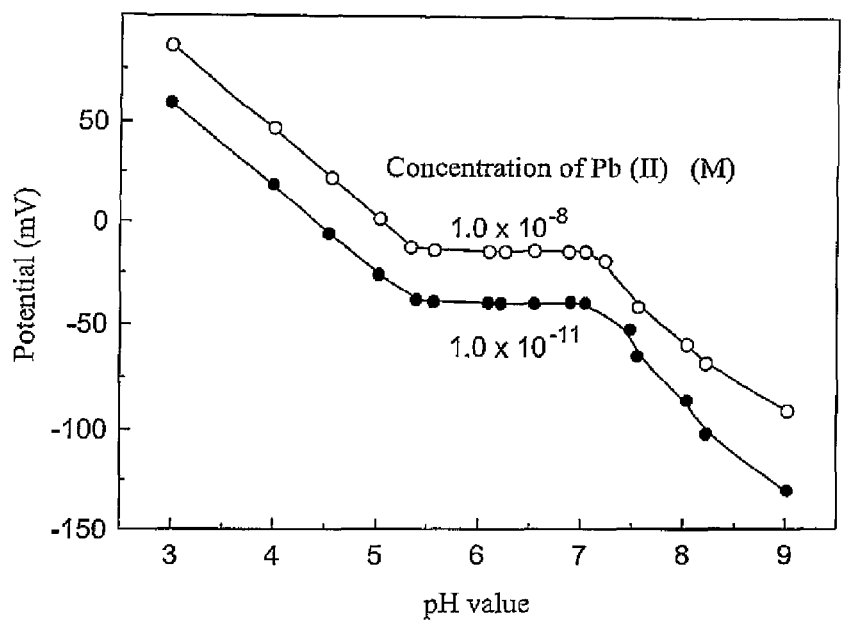
FIG. 5 shows pH dependence of the potentiometric sensor.

Response time of the sensor was determined and shown in FIG. 4. As show in FIG. 4, the sensor has quick response time of about 37 seconds. pH dependence of the sensor was also measured and an adequate pH window (FIG. 5) from pH 5.5 to pH 7.0 were determined (FIG. 5).

The example show that the potentiometric Pb(II) sensors disclosed herein can allow quick, reliable and sensitive detection of Pb(II) in a sample.

Example 6

Selectivity of the Potentiometric Pb(II) Sensor to Pb(II)

Figure 6:
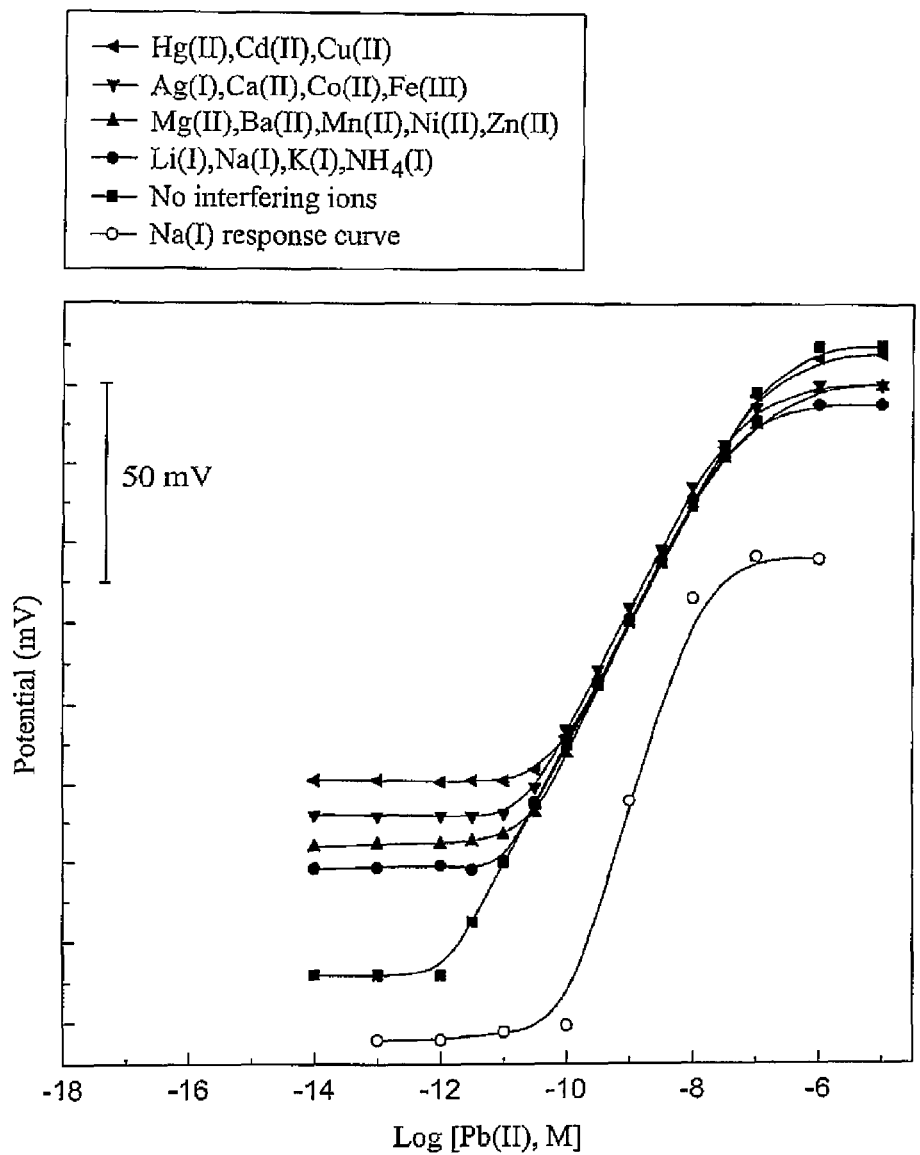
FIG. 6 shows response curves of the potentiometric sensor by fixed interference method at an interfering ion concentration of $1.0 \times 10^{-9}$ M.

Potentiometric Pb(II) sensors were assembled using the typical procedure described in Example 3. Selectivity of the potentiometric Pb(II) sensors to Pb(II) ions were measured over various interfering ions in a mixed solution by fixed interference method. In the mixed solution, the interfering ions were at a fixed concentration of $1.0 \times 10^{-9}$ M. The results are shown in FIG. 6. As shown in FIG. 6, the sensor showed good selectivity towards Pb(II) against 16 types of interfering ions. And the sensor shows good are selective towards Pb(II) ion against all alkaline metal ions examined since all of the lower detection limits only shifted up 1 order of magnitude. Even in the presence of Hg(II), Cd(II) and Cu(II) that have similar complex abilities to Pb(II), the lower detection limit just shifted up 1.92 order of magnitudes.

Figure 7:
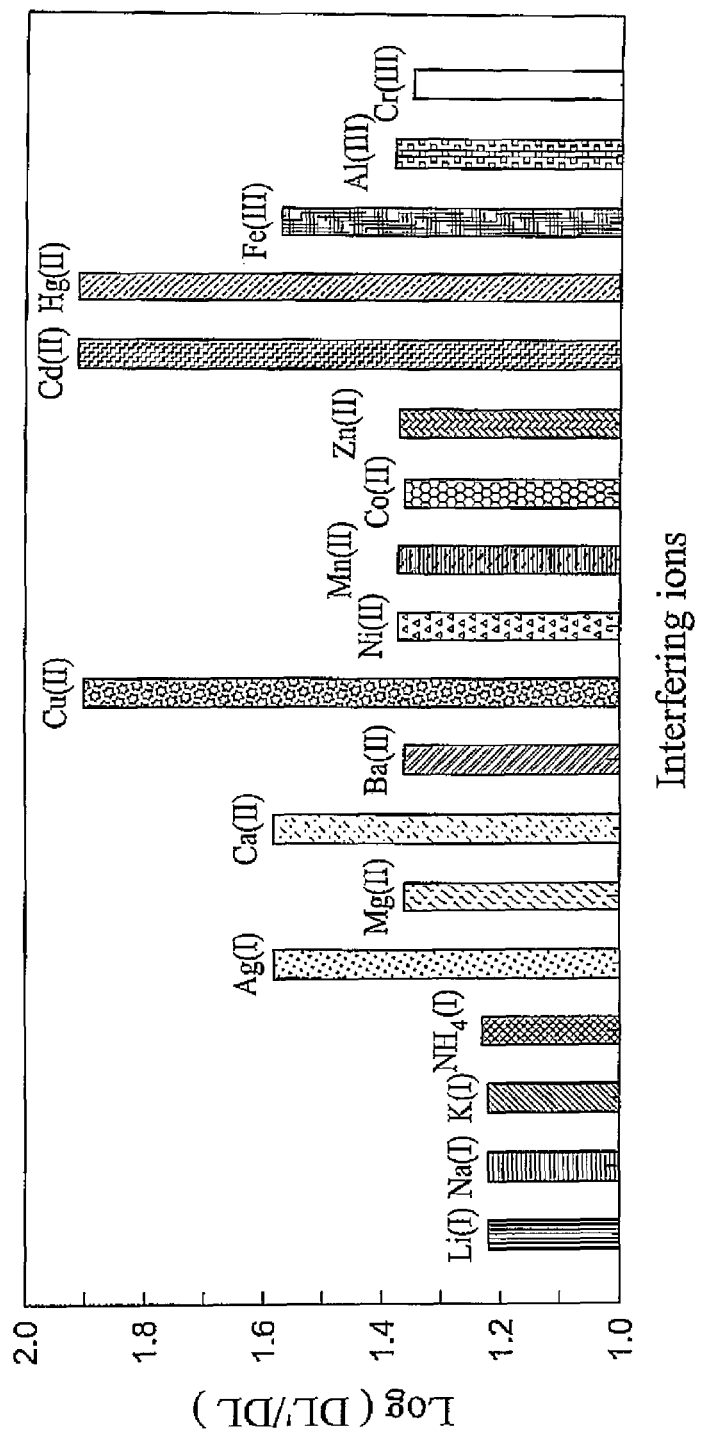
FIG. 7 shows changes in the lower detection limit for the potentiometric sensor in the presence of various interfering ions.

FIG. 7 quantitatively describes changes in the lower detection limit for the sensor in the presence of interfering ions. As shown in FIG. 7, the lower detection limit for the sensor shifted up merely 1.92 order of magnitude in the presence of various interfering ions. This example demonstrates that the potentiometric Pb(II) sensor is highly selective for Pb(II) ions.

Example 7

Evaluation of Lifetime and Regenerability of the Potentiometric Pb(II) Sensor

Potentiometric Pb(II) sensors were assembled using the typical procedure described in Example 3.

Figure 8:
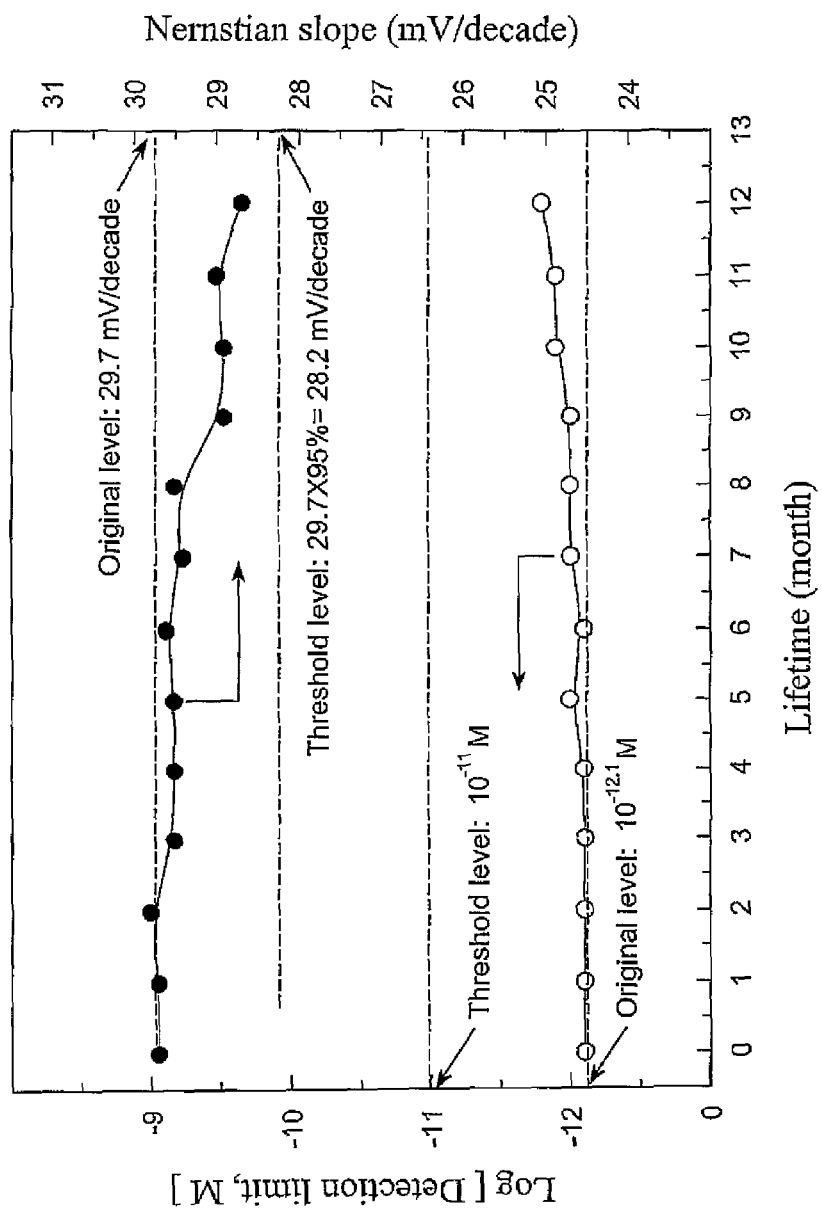
FIG. 8 shows variations in the lower detection limit and Nernstian slope of the potentiometric sensor.

Operating lifetime of the sensors was evaluated in standard $Pb(NO_3)_2$ solution by inspecting variation of calibration curve at a using frequency of twice a week. The sensor was storied in $1.0 \times 10^{-4}$ M $Pb(NO_3)_2$ solution in a dark place when it was not used. Before every use, the electrode was washed with deionized water until a stable potential was reached. The observed calibration curves are shown in FIG. 8. From the calibration curves obtained, the variations of the lower detection limit and Nernstian slope of the sensor were determined.

As shown in FIG. 8, the detection limit of the sensor only moved up to $10^{-11.8}$ M, which represents only 0.3 order of magnitude relative to the original value, at the end of the one-year examination period. Meanwhile, the Nernstian slope of the sensor was still 96.6% of the original Nernstian slope at the end of the one-year examination period, which is well above the 95% threshold required for the sensor to be considered usable in lead detection.

This example demonstrates that the potentiometric Pb(II) sensor has a long operating lifetime.

Example 8

Sensitivity of the Potentiometric Pb(II) Sensor to Pb(II)

A whole blood sample was collected from a healthy volunteer and used as "an analytical blank" to establish the method detection limit (MDL) and the method quantification limit (MQL) for lead level in blood samples. A precise volume of blood of 60 μl, was drawn by fingerstick from a clean finger of the volunteer and transferred into a vessel to undergo digestion immediately. The digested solution was set at constant volume of 500 mL.

Potentiometric Pb(II) sensors were assembled using the typical procedure described in Example 3 and used for detecting lead level in various samples. The blank value in blood was determined by the potentiometric sensor via Gran's plot. The method detection limit $3\sigma$ and the method quantification limit $10\sigma$ were calculated from the standard deviation $\sigma$, respectively (Table 1). Deionized water was also selected as a blank to determine method limits. A precise volume of deionised water of 150 μl was digested like blood and then set at constant volume of 100 mL. The determined MDLs and MQLs are summarized in Table 1.

TABLE 1

Determination of detection and quantification limits of the method via Gran's plot

| Analytical blank sample | Background value of lead in digested solution (M) | Background value of lead in blood (μg/L) | Average background value (μg/L) | Standard deviation (μg/L) | Method limit |
|---|---|---|---|---|---|
| Human whole blood without lead | $1.318 \times 10^{-12}$ | 2.274 | 2.05 | 0.262 | MDL $3\sigma$ = 0.79 μg/L |
| | $1.413 \times 10^{-12}$ | 2.437 | | | MQL $10\sigma$ = 2.6 μg/L |
| | $1.023 \times 10^{-12}$ | 1.765 | | | |
| | $1.175 \times 10^{-12}$ | 2.027 | | | |
| | $1.148 \times 10^{-12}$ | 1.980 | | | |
| | $1.047 \times 10^{-12}$ | 1.780 | | | |
| | $1.230 \times 10^{-11}$ | 1.697 | | | |
| | $1.130 \times 10^{-11}$ | 1.559 | | | |
| Deionized water | $1.175 \times 10^{-11}$ | 1.622 | 1.63 | 0.0961 | MDL $3\sigma$ = 0.29 μg/L |
| | $1.089 \times 10^{-11}$ | 1.503 | | | MQL $10\sigma$ = 0.96 μg/L |
| | $1.186 \times 10^{-11}$ | 1.637 | | | |
| | $1.285 \times 10^{-11}$ | 1.773 | | | |

This example shows that the potentiometric Pb(II) sensor disclosed herein can offer sensitive detection of lead ions in samples.

Example 9

Spiked Recovery Experiment

Potentiometric Pb(II) sensors were assembled using the typical procedure described in Example 3 and used for detecting lead level in spiked samples. Recovery of 6 replicates for spiking blood lead within a range corresponding to about 1-3 times of the background value were conducted to evaluate the lowest level of method validation (LLMV). For spiking levels at 2.07 μg/L, 3.45 μg/L, and 6.21 μg/L, the analyte recovery and relative standard deviation (RSD) was about 106%~110% and 2%~7%, indicating an excellent accuracy and precision.

This example shows that the LLMV of the Pb(II) potentiometric sensor disclosed herein is about 2 μg/L, which is superiors to ASV and comparable with graphite furnace atomic absorption spectrometry (GFAAS).

Potentiometric Pb(II) sensors were assembled using the typical procedure described in Example 3.

Example 10

Detection of Pb(II) in Whole Blood Samples

In this example, potentiometric Pb(II) sensors were assembled using the typical procedure described in Example 3 and used for detecting lead level in various whole blood samples.

Collection and Process of Blood Samples

Six whole blood samples were collected from vein in arm of patients shown symptoms suggesting lead poisoning by venipuncture at the Huaxi Second Hospital affiliated to Sichuan University, Sichuan, China. Anticoagulant sodium citrate was added to each of the blood samples. Two additional whole blood samples were collected as control samples from vein in an aim of a 24-year-old healthy volunteer twice (1.5 hours after a normal meal and 1.5 hours after having 150 g puffed food). The control blood samples were directly used to assay Pb(II) concentration without adding any anticoagulant. The blood samples were then digested by 3.0M $HNO_3$ and 30% $H_2O_2$. Each of the digested samples was transferred to 100 mL or 500 mL volumetric flask. The volume was set to the mark with deionized water.

Blood Assay

Lead concentrations in the blood samples were detected using the potentiometric Pb(II) sensors and graphite furnace atomic absorption spectrometry (GFAAS). The results obtained using GFAAS were used as true values for calculation of relative error. The Pb(II) concentration of each of the digested blood sample was based on the average of nine replicate tests analyzed by the potentiometric Pb(II) sensors using the method of standard additions in Gran's plot way. Average Pb(II) concentration (after deduction of background value) ($\overline{C}$), relative error (RE), and relative standard deviation (RSD) of lead concentration in blood were respectively calculated according to the following equations:

$$\overline{C}=(C_1+C_2+C_3+\ldots+C_n)/n$$

$$RSD=\{[(C_1-\overline{C})^2+(C_2-\overline{C})^2+\ldots+(C_n-\overline{C})^2]/(n-1)\}^{1/2}/\overline{C}$$

Relative error (%)=$(\overline{C}-C_{AAS})/C_{AAS}$

Summary of the results from the blood assays obtained from using the potentiometric Pb(II) sensor and clinical methods are shown in Table 2.

TABLE 2

Performance comparison of the potentiometric Pb(II) sensor and current clinical methods

| | Clinical analysis | | Analysis by the potentiometric sensor | | | |
|---|---|---|---|---|---|---|
| Method | Blood lead level (μg/L) | Blood volume (μL) | Lead conc. in digestedsolution at fixed volume (×$10^{-10}$M) | Blood lead level (μg/L) | RSD (%) | Relative error (%) |
| GFAAS, ASV | <20[a] | 150 | 0.135 | <20[b] | — | — |
| GFAAS | 27.8 | 150 | 2.24 | 28.9 | 4.10 | +4.00 |
| GFAAS | 45.6 | 150 | 3.70 | 49.1 | 3.39 | +7.68 |
| GFAAS | 53.4 | 150 | 4.30 | 57.3 | 4.40 | +7.30 |
| GFAAS | 77.6 | 150 | 6.11 | 82.3 | 4.67 | +6.06 |
| GFAAS | 89.7 | 150 | 7.24 | 97.8 | 7.34 | +9.14 |
| GFAAS | 85.8 | 50 | 2.24 | 90.9 | 3.77 | +5.94 |

[a]Clinical analysis failed to detect the blood lead level because the lead level in the sample was lower than the method detection limit of 20 μg/L.
[b]The test results are beyond the lowest level of method validation (LLMV) of 2 μg/L.

As shown in Table 2, for human blood having a lead level over 20 μg per liter, both RSD for 9 times determination and relative errors are below 7.34% and 9.59%, which presents a repeatable and reliable measurement by the potentiometric Pb(II) sensor. Even for those blood samples that the clinical analysis in hospital failed to detect the presence of lead (i.e., the blood samples having lead level lower than 20 μg/L), the potentiometric Pb(II) sensor can still detect and measure the lead amount in the samples and give the more narrow range of lower than 5 μg/L. Since as high as RSD of 20% and relative error of 20% are acceptable in trace amount quantitative analysis, the results in Table 2 demonstrate that the potentiometric Pb(II) sensor disclosed herein can be used to accurately and reliably detect lead level in blood.

Further, the potentiometric sensors were used to evaluate the harm of puffed foods to human body by measuring the blood lead level of a man after lead exposure via eating commercial puffed foods that were believed to be contaminated by lead. The results show that the blood lead level rapidly increased from <2 μg/L to 90.9 μg/L (Table 2).

This example demonstrates that the potentiometric sensor can be used clinically as a reliable and sensitive screening and measuring method for lead exposure in blood.

Example 11

Evaluation of Lifetime and Regenerability of the Potentiometric Pb(II) Sensor

Potentiometric Pb(II) sensors were assembled using the typical procedure described in Example 3.

In order to examine the validity of the sensor, the calibration curve of the sensor was monitored during the usage of the sensor for detecting blood lead level. Operating lifetime of the sensors was evaluated in standard $Pb(NO_3)_2$ solution by inspecting variation of calibration curve at a using frequency of once everyday. The sensor was storied in $1.0\times10^{-4}$ M $Pb(NO_3)_2$ solution in a dark place when it was not used. Before every use, the electrode was washed with deionized water until a stable potential was reached. The recorded response potential was repeated at least three times. The results are shown in Table 3. The variation of potential response curves for Pb(II) in $Pb(NO_3)_2$ standard solution of the sensor during processes of usage for Pb(II) assays in biological systems is shown in FIG. 9.

Figure 9:
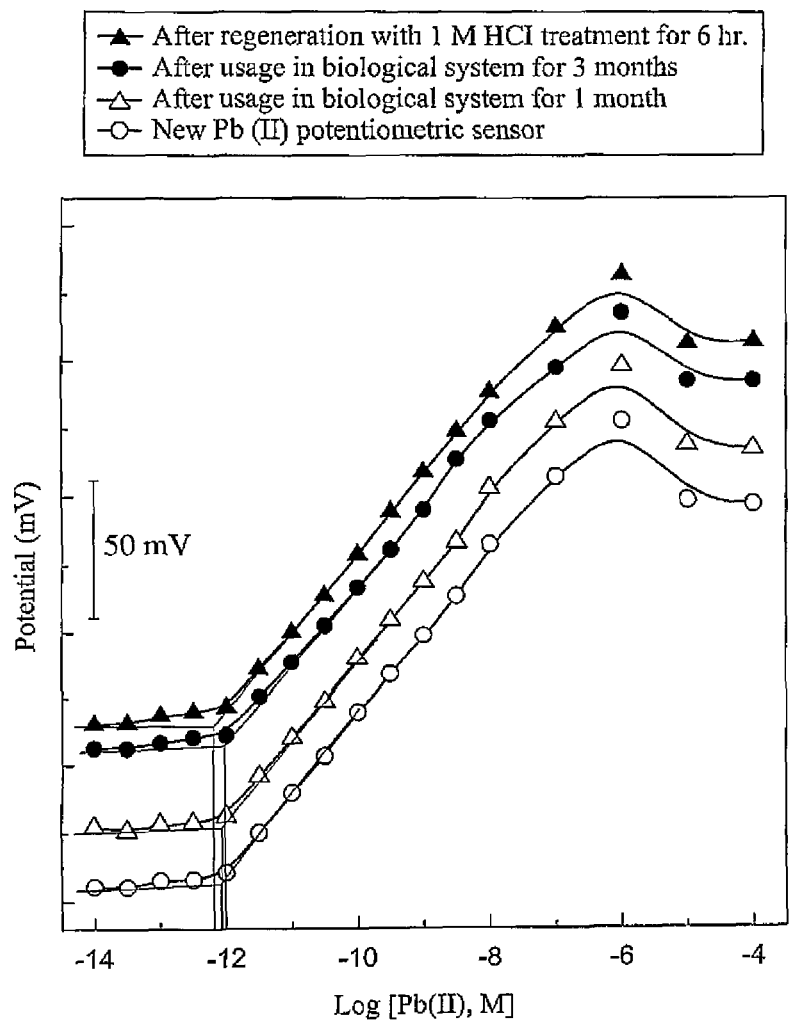
FIG. 9 shows variations of potential response curves for Pb(II) in Pb(NO$_3$)$_2$ standard solution during the process of usage for Pb(II) assay in biological systems and regeneration of sensor.

As shown in Table 3 and FIG. 9, the potentiometric Pb(II) sensors maintained its Pb(II) response after being used in the biological systems for 1 month. After usage in the biological systems for 3 months, no obvious deterioration in the lower detection limit was observed, but the slope decreased from 29.6 mV/decade to 28.1 mV/decade (which is exactly 95% to the original slope value 29.6 mV/decade).

TABLE 3

Variation in parameters of the sensor during the usage for Pb(II) assays in biological systems and regeneration

| Parameters of the sensor | New sensor | After usage in biological systems for 1 month | After usage in biological systems for 3 months | After regeneration with 1M HCl treatment for 6 hours |
|---|---|---|---|---|
| Working range (M) | $10^{-12.1}$-$10^{-6.0}$ | $10^{-12.1}$-$10^{-6.0}$ | $10^{-12.0}$-$40^{-6.0}$ | $10^{-12.2}$-$10^{-60}$ |
| Correlation coefficient* | 0.9995 | 0.9995 | 0.9986 | 0.9996 |
| Slope (mV/decade)* | 29.7 | 29.7 | 28.1 | 28.7 |
| Detection limit (M) | $10^{-12.1}$ | $10^{-12.1}$ | $10^{-12.0}$ | $10^{-12.2}$ |

*These two parameters were obtained from fitting linear analysis of the response curves in the Pb(II) concentration range from $10^{-12}$M to $10^{-7}$M.

This Example shows that the potentiometric Pb(II) sensor has a long operating lifetime and can be regenerated.

Example 12

Performance Comparison of the Potentiometric Pb(II) Sensor and Other Pb(II) Sensors This example provides a summary comparing the performance of the potentiometric Pb(II) sensor disclosed herein and some other currently available Pb(II) sensors.

TABLE 4

Comparison of performance of non-limiting examples of the potentiometric Pb(II) sensors disclosed herein with other Pb(II) sensors with advanced detection limit

| Composition of sensing membrane | Slope (mV/decade) | Working range (M) | Response time | Lifetime (month) |
|---|---|---|---|---|
| Polypyrrole copolymer/vinyl polymer | 29.7 | $7.9 \times 10^{-13}$-$1.0 \times 10^{-6}$ ($10^{-12.1}$-$1.0 \times 10^{-6}$) | 37 seconds | 12 |
| ETH5435 dissolved in DOS-PVC membrane | 29 ± 1 | $1.0 \times 10^{-11}$-$1.0 \times 10^{-3}$ | 15-30 minutes | One week |
| ETH5234 dissolved in DOS-PVC membrane | 29.6 | $3.0 \times 10^{-9}$-$1.0 \times 10^{-4}$ | 10 minutes | One week |
| Diphenylmethyl-N-phenylhydroxamic acid dissolved in DBP-SAN cyanocopolymer membrane | 36.7 | $7.4 \times 10^{-8}$-$3.7 \times 10^{-1}$ | 13 seconds | 6 |
| 5,5-Dithiobis(2-nitrobenzoic acid dissolved in DBP-PVC membrane | 29.1 ± 0.4 | $1.0 \times 10^{-9}$-$1.0 \times 10^{-3}$ | 7-10 seconds | 3 |

This example shows that the potentiometric Pb(II) sensor has superior performance over various currently available Pb(II) sensors.

In at least some of the previously described embodiments, one or more elements used in an embodiment can interchangeably be used in another embodiment unless such a replacement is not technically feasible. It will be appreciated by one of ordinary skill in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, one of ordinary skill in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, one of ordinary skill in the art will recognize that the disclosure is also thereby described in terms of any individual member or subgroup of members of the Markush group.

As will be understood by one of ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one of ordinary skill in the art all language such as "up to," "at least," "greater than," "less than," and the like include the number recited and refer to ranges which can be subsequently broken down into sub-ranges as discussed above. Finally, as will be understood by one of ordinary skill in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to one of ordinary skill in the art. The various aspects and embodiments disclosed herein are for purposes of illustration and are not intended to be limiting, with the true scope and spirit being indicated by the following claims.

One of ordinary skill in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

What is claimed is:

1. A composition comprising a polypyrrole copolymer and a vinyl polymer, wherein the polypyrrole copolymer comprises at least one optionally substituted pyrrole as a first monomer unit and at least one optionally substituted 2-hydroxy-5-sulfonic aniline as a second monomer unit; and the vinyl polymer is a terpolymer of vinyl chloride, vinyl acetate and hydroxyalkyl acrylate.

2. The composition of claim 1, wherein the first monomer unit is represented by Formula I:

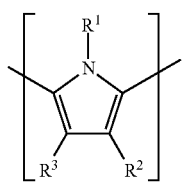

(I)

wherein $R^1$, $R^2$, and $R^3$ are each independently selected from the group consisting of hydrogen, halogen, $C_{1-6}$ alkyl, cycloalkyl, aryl, alkylenyl, and alkoxyl.

3. The composition of claim 2, wherein $R^1$, $R^2$, and $R^3$ are each independently hydrogen.

4. The composition of claim 2, wherein $R^2$ and $R^3$ are the same.

5. The composition of claim 1, wherein the second monomer unit is represented by Formula II:

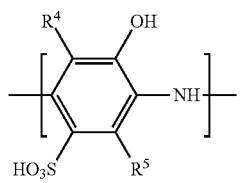

(II)

wherein $R^4$ is hydrogen or an electron-donating group, and $R^5$ is hydrogen or an electron-donating group.

6. The composition of claim 5, wherein $R^4$ and $R^5$ are each independently hydrogen.

7. The composition of claim 5, wherein the electron-donating group is $C_{1-6}$ alkyl or alkoxyl.

8. The composition of claim 1, wherein the polypyrrole copolymer comprises at least about 10% of the first monomer unit by mole.

9. The composition of claim 1, wherein the polypyrrole copolymer comprises about 50% of the first monomer unit by mole.

10. The composition of claim 1, wherein the polypyrrole copolymer has a molar ratio of the first monomer unit to the second monomer unit from about 10:90 to about 90:10.

11. The composition of claim 1, wherein the polypyrrole copolymer has a molar ratio of the first monomer unit to the second monomer unit of about 50:50.

12. The composition of claim 1, wherein the polypyrrole copolymer is present as nanoparticles.

13. The composition of claim 12, wherein the nanoparticles have an average size of about 20 nm to about 450 nm.

14. The composition of claim 12, wherein the nanoparticles have an average size of about 60 nm to about 100 nm.

15. The composition of claim 1, wherein the composition is in the form of a film, a membrane, a foil, or a combination thereof.

16. The composition of claim 1, wherein the vinyl polymer comprises about 50% to about 90% vinyl chloride by weight.

17. The composition of claim 1, wherein the vinyl polymer comprises about 3% to about 50% vinyl acetate by weight.

18. The composition of claim 1, wherein the composition is substantially plasticizer-free.

19. A polymeric membrane for ion sensitive measurement comprising a vinyl polymer and a polypyrrole copolymer, wherein the polypyrrole copolymer comprises at least one optionally substituted pyrrole as a first monomer unit and at least one optionally substituted 2-hydroxy-5-sulfonic aniline as a second monomer unit; and the vinyl polymer is a terpolymer of vinyl chloride, vinyl acetate and hydroxyalkyl acrylate.

20. The polymeric membrane of claim 19, wherein the first monomer unit is represented by Formula I:

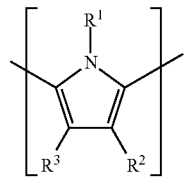

(I)

wherein $R^1$, $R^2$, and $R^3$ are each independently selected from the group consisting of hydrogen, halogen, $C_{1-6}$ alkyl, cycloalkyl, aryl, alkylenyl, and alkoxyl.

21. The polymeric membrane of claim 19, wherein the second monomer unit is represented by Formula II:

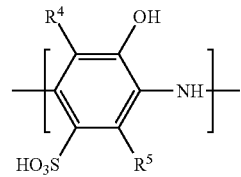

(II)

wherein $R^4$ is hydrogen or an electron-donating group, and $R^5$ is hydrogen or an electron-donating group.

22. The polymeric membrane of claim 19, wherein the polymeric membrane has about 0.1% to about 10% the polypyrrole copolymer by weight.

23. The polymeric membrane of claim 19, wherein the polymeric membrane has about 3% the polypyrrole copolymer by weight.

24. The polymeric membrane of claim 19, wherein the polymeric membrane comprises one or more ion exchangers.

25. The polymeric membrane of claim 24, wherein the polymeric membrane has about 0.1% to about 10% the one or more ion exchangers by weight.

26. The polymeric membrane of claim 24, wherein the one or more ion exchangers are selected from the group consisting of sodium tetraphenylborate (NaTPB), potassium tetraphenylborate (KTPB), potassium tetrakis(4-chlorophenyl)]borate (KTClPB), potassium tetrakis[3,5-bis(trifluoromethyl) phenyl]borate (KTFPB), sodium tetrakis[3,5-bis(trifluoromethyl)phenyl]borate (NaTFPB), sodium tetrakis[3,5-bis(perfluorohexyl)phenyl]borate (NaPFHPB), and any combination thereof.

27. The polymeric membrane of claim 19, wherein the polymeric membrane has an average thickness of about 40 μm to about 200 μm.

28. The polymeric membrane of claim 19, wherein the polymeric membrane has an average thickness of about 120 μm.

29. The polymeric membrane of claim 28, wherein the ion sensitive measurement is a potentiometric measurement.

30. The polymeric membrane of claim 19, wherein the polymeric membrane has an operating lifetime of more than about 1 month.

31. The polymeric membrane of claim 19, wherein the polymeric membrane has an operating lifetime of more than about 3 months.

32. The polymeric membrane of claim 19, wherein the polymeric membrane has an operating lifetime of more than about 6 months.

33. A sensor for measuring lead ions, the sensor comprising: a lead ion-selective electrode, wherein the lead ion-selective electrode comprises a vinyl polymer and a polypyrrole copolymer, wherein the polypyrrole copolymer comprises at least one optionally substituted pyrrole as a first monomer unit and at least one optionally substituted 2-hydroxy-5-sulfonic aniline as a second monomer unit; and the vinyl polymer is a terpolymer of vinyl chloride, vinyl acetate and hydroxyalkyl acrylate.

34. The sensor of claim 33, wherein the lead ion-selective electrode comprises one or more ion exchangers.

35. The sensor of claim 33, wherein the sensor further comprises a reference electrode.

36. A method for detecting lead ions in a sample, the method comprising:
providing a sample suspected of containing one or more lead ions;
contacting the sample with a sensor, wherein the sensor comprises a reference electrode and a lead ion-selective electrode, wherein the lead ion-selective electrode comprises a vinyl polymer and one or more ionophores selective for lead ions; and
measuring an electromotive force (EMF) between the reference electrode and the lead ion-selective electrode,
wherein the one or more ionophores comprise a polypyrrole copolymer, wherein the polypyrrole copolymer comprises at least one optionally substituted pyrrole as a first monomer unit and at least one optionally substituted 2-hydroxy-5-sulfonic aniline as a second monomer unit; and the vinyl polymer is a terpolymer of vinyl chloride, vinyl acetate and hydroxyalkyl acrylate.

37. The method of claim 36, wherein the sensor is potentiometric and functions substantially logarithmic.

38. The method of claim 36, wherein the concentration of lead ions in the sample correlates with the EMF measured.

39. The method of claim 38, wherein the concentration of lead ions in the sample positively correlates with the EMF measured.

40. The method of claim 36, wherein the measured EMF is greater in the presence of lead ions than in the absence of lead ions.

41. The method of claim 36, wherein the concentration of the lead ions in the sample is about $10^{-6}$M to about $10^{-13}$M.

42. The method of claim 36, wherein the concentration of the lead ions in the sample is about $10^{-9}$M to about $10^{-13}$M.

43. The method of claim 36, wherein the concentration of the lead ions in the sample is about $7.9 \times 10^{-13}$ M.

44. The method of claim 36, wherein the sample is contacted with the sensor for no more than about 60 minutes.

45. The method of claim 36, wherein the sample is contacted with the sensor for no more than about 20 minutes.

46. The method of claim 36, wherein the sample is a biological sample.

47. The method of claim 46, wherein the biological sample is selected from the group consisting of whole blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, a biopsy sample, and any combination thereof.

48. The method of claim 36, wherein the sample is a blood sample.

49. The method of claim 36, further comprising contacting the sensor with a regenerating agent to form a regenerated sensor.

50. The method of claim 49, further comprising contacting a second sample suspected of containing lead ions with the regenerated copolymer.

51. The method of claim 49, wherein the regenerating agent is selected from the group consisting of hydrochloric acid, nitric acid, sulfuric acid, and any combination thereof.

52. An apparatus for measuring lead ions, the apparatus comprising: a polymeric membrane comprising a vinyl polymer, a polypyrrole copolymer and one or more ion exchangers, wherein the polypyrrole copolymer comprises at least one optionally substituted pyrrole as a first monomer unit and at least one optionally substituted 2-hydroxy-5-sulfonic aniline as a second monomer unit; and the vinyl polymer is a terpolymer of vinyl chloride, vinyl acetate and hydroxyalkyl acrylate.

53. The apparatus of claim 52, wherein the first monomer unit is represented by Formula I:

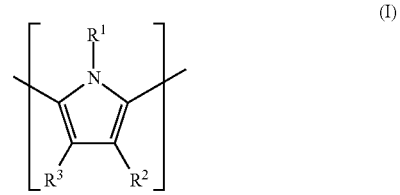

wherein $R^1$, $R^2$, and $R^3$ are each independently selected from the group consisting of hydrogen, halogen, $C_{1-6}$ alkyl, cycloalkyl, aryl, alkylenyl, and alkoxyl.

54. The apparatus of claim 52, wherein the second monomer unit is represented by Formula II:

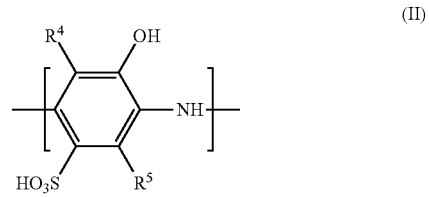

(II) wherein $R^4$ is hydrogen or an electron-donating group, and $R^5$ is hydrogen or an electron-donating group.

55. The apparatus of claim 52, wherein the polymeric membrane has about 0.1% to about 10% the polypyrrole copolymer by weight.

56. The apparatus of claim 52, wherein the polymeric membrane has about 0.1% to about 10% the one or more ion exchangers by weight.

57. The apparatus of claim 52, wherein the one or more ion exchangers are selected from the group consisting of sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl]borate (NaTFPB), sodium tetrakis [3,5-bis(perfluorohexyl)phenyl]borate (NaPFHPB), and any combination thereof.

58. The apparatus of claim 52, wherein the polymeric membrane has an average thickness of about 40 μm to about 200 μm.

59. The apparatus of claim 52, wherein the polymeric membrane has an average thickness of about 120 μm.

60. The apparatus of claim 52, wherein the polymeric membrane has an operating lifetime of more than about 1 month.

61. The apparatus of claim 52, wherein the polymeric membrane has an operating lifetime of more than about 3 months.

\* \* \* \* \*

UNITED STATES PATENT AND TRADEMARK OFFICE
CERTIFICATE OF CORRECTION

Page 1 of 2

PATENT NO. : 8,845,905 B2
APPLICATION NO. : 13/821391
DATED : September 30, 2014
INVENTOR(S) : Huang et al.

It is certified that error appears in the above-identified patent and that said Letters Patent is hereby corrected as shown below:

On the Title Page

On Page 2, Item (56), under "OTHER PUBLICATIONS", in Column 1, Line 6, delete "Baseed" and insert -- Based --, therefor.

On Page 2, Item (56), under "OTHER PUBLICATIONS", in Column 2, Line 2, delete "choronopotentiometry" and insert -- chronopotentiometry --, therefor.

On Page 2, Item (56), under "OTHER PUBLICATIONS", in Column 2, Line 31, delete "Eletrolyte" and insert -- Electrolyte --, therefor.

In the Specification

In Column 3, Line 36, delete "1 months." and insert -- 1 month. --, therefor.

In Column 7, Line 66, delete "zero, on;" and insert -- zero, one, --, therefor.

In Column 13, Line 1, delete "YMCA," and insert -- VMCA, --, therefor.

In Column 16, Line 13, delete "Various electrode" and insert -- Various electrodes --, therefor.

In Column 20, Line 9, delete "diaphram" and insert -- diaphragm --, therefor.

In Column 20, Line 10, delete "diaphramor" and insert -- diaphragm --, therefor.

In Column 20, Line 36, delete "(EMP)" and insert -- (EMF) --, therefor.

In Column 20, Line 39, delete "solution)|$Hg_2Cl_2$|Hg" and insert -- solution)|$Hg_2Cl_2$|Hg. --, therefor.

Signed and Sealed this
Tenth Day of March, 2015

Michelle K. Lee
*Deputy Director of the United States Patent and Trademark Office*

CERTIFICATE OF CORRECTION (continued)
U.S. Pat. No. 8,845,905 B2

In Column 21, Line 1, delete "Pb(H)" and insert -- Pb(II) --, therefor.

In Column 23, Line 8, delete "an aim" and insert -- an arm --, therefor.

In Column 23, Line 46, in Table 2, delete "digestedsolution" and insert -- digested solution --, therefor.

In Column 26, Line 19, delete "A, 13," and insert -- A, B, --, therefor.